(12) United States Patent
Fischer et al.

(10) Patent No.: US 7,026,341 B2
(45) Date of Patent: Apr. 11, 2006

(54) HETARYL SUBSTITUTED HOMOTETRAMIC AND HOMOTETRONIC ACIDS AND THEIR USE THEREOF AS PESTICIDES

(75) Inventors: Reiner Fischer, Monheim (DE); Astrid Ullmann, Köln (DE); Axel Trautwein, Bergisch Gladbach (DE); Mark Wilhelm Drewes, Langenfeld (DE); Christoph Erdelen, Leichlingen (DE); Peter Dahmen, Neuss (DE); Dieter Feucht, Monheim (DE); Rolf Pontzen, Leichlingen (DE); Peter Lösel, Leverkusen (DE)

(73) Assignee: Bayer CropScience AG, Monheim (DE)

( * ) Notice: Subject to any disclaimer, the term of this patent is extended or adjusted under 35 U.S.C. 154(b) by 98 days.

(21) Appl. No.: 10/450,933

(22) PCT Filed: Dec. 21, 2001

(86) PCT No.: PCT/EP01/15258

§ 371 (c)(1),
(2), (4) Date: Nov. 24, 2003

(87) PCT Pub. No.: WO02/062791

PCT Pub. Date: Aug. 15, 2002

(65) Prior Publication Data

US 2004/0097558 A1    May 20, 2004

(30) Foreign Application Priority Data

Jan. 4, 2001    (DE) ................................ 101 00 175

(51) Int. Cl.
*A01N 43/78*    (2006.01)
*C07D 277/20*    (2006.01)

(52) U.S. Cl. ..................... 514/365; 504/266; 548/202; D22/120

(58) Field of Classification Search ............... 548/202; 514/365; 504/266; D22/120
See application file for complete search history.

(56) References Cited

U.S. PATENT DOCUMENTS

| | | | |
|---|---|---|---|
| 3,538,107 A | 11/1970 | Hepworth et al. ........... 260/302 |
| 3,749,787 A | 7/1973 | Hepworth et al. ........... 424/270 |
| 5,084,083 A | 1/1992 | Lewis et al. .................... 71/90 |
| 5,789,440 A | 8/1998 | Ellsworth et al. ........... 514/460 |
| 5,840,751 A | 11/1998 | Ellsworth et al. ........... 514/460 |
| 5,936,128 A | 8/1999 | Ellsworth et al. ............. 568/67 |
| 6,028,033 A | 2/2000 | Hill et al. .................... 504/244 |
| 6,071,937 A | 6/2000 | Bretschneider et al. ..... 514/336 |

FOREIGN PATENT DOCUMENTS

| | | |
|---|---|---|
| EP | 0 328 954 | 8/1989 |
| EP | 0 885 885 | 12/1998 |
| JP | 8-325230 | 12/1996 |
| JP | 11-152273 | 6/1999 |

OTHER PUBLICATIONS

Djudjic et al., Org. Preparations and Procedures Intl., (1985), vol. 17, No. 3, pp. 206-210.*
Lacan et al., Acta Pharmaceutical Jugoslavica, (1981), vol. 31, No. 1, pp. 47-51.*
Arch. Pharm. 309, (month unavailable) 1976, pp. 558-565, "Zur Synthese von Kawalactonderivaten" by A. M. Chirazi et al.
J. Amer. Chem. Soc., 93, Jan. 31, 1971, pp. 281-282, "Darzens Condensation of α-Haloactones: Glycidic Lactones as Intermediates in Acetogenin Synthesis" by J. D. White et al.
Chemical Reviews, vol. 52, (month unavailable) 1953, pp. 237-416.
Indian J. Chem, vol. 6, Jul. 1968, pp. 341-345, Isoquinoline Derivates: Part XVIII-Formation of I-Alkyl-(or Alkaryl or aryl)-3-methyl-7-chloro-(or 5-chloro)-isoquinolines by B. Bhattacharya.
Chem. Ind (London), Nov. 9, 1968, p, 1568, "Use of molecular sieves in the methyl esterification of carboxylic acids" by H. R. Harrison et al.

(Continued)

*Primary Examiner*—Taofiq Solola
(74) *Attorney, Agent, or Firm*—Richard E. L. Henderson; Raymond J. Harmuth

(57) ABSTRACT

The present invention relates to new hetaryl-substituted homotetramic and homotetronic acids of the formula (I)

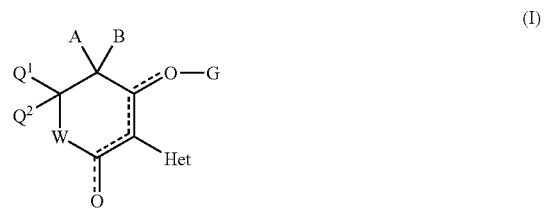

in which
A, B, $Q^1$, $Q^2$, W, G and Het have the meanings stated in the disclosure,
to a plurality of processes for their preparation, and to their use as pesticides, microbicides, and herbicides.

11 Claims, No Drawings

OTHER PUBLICATIONS

Organikum [Organic Chemistry], VEB Deutcher Verlag der Wissenschaften, (month unavailable) Berlin 1977, pp. 505-507, D.7.1.5. Reaktionen von Carbonsäuren und Carbonsäurederivaten mit Basen.

H. Henecka, Houben-Weyl, Methoden der Organischen Chemie, [Methods in Organic Chemistry], (month unavailable) 1952, vol. 8, pp. 467-469, "Isoanthraflavinsäure; Morpholchinon".

Chem. Parm. Bull. 46 (7), pp. 1116-1124, (month unavailable) 1998, "Novel 5-Hydroxytryptamine 4 (5-HT$_4$) Receptor Agonist Synthesis and Gastroprokinetic Activity of 4-Amino-*M*-[2-(1-aminocycloalkan-1-yl)ethyl]-5-chloro-2-methoxybenzamides" by T. Suzuki et al.

Organikum, VEB Deutscher Verlag der Wissenschaften, (month unavailable) Berlin 1990, 18th ed. pp. 501-502, "D.7.3.5. Reaktionen mit metallorganischen Verbindungen".

Chem. Ind., 37, (month unavailable) 1985, pp. 730-732, "Schiffsfarben—eine Spezialitäder seenahen Lackindustrie" by H. R. Ungerer.

J. Med. Chem., (month unalailable) 1983, 26, pp. 700-714, "Inhibitors of Glycolic Acid Oxidase. 4-Substituted 3-Hydroxy-1*H*-pyrrole-2,5-dione Derivatives" by C. S. Rooney et al.

J. Med. Chem. (month unavailable) 1996, 39, pp. 237-245, "Azole Phenoxy Hydroxyureas as Selective and Orally Active Inhibitors of 5-Lipoxygenase" by M. S. Malamas.

J. Med. Chem., (month unavailable) 1998, 41, pp. 5037-5054, *N*-(2-Benzoylphenyl)-L-tyrosine PPARy Agonists. 1. Structure-Activity Relationship and Opitimization of the Phenyl Alkyl Ether Moiety by J. L. Collins et al.

Synthetic Communications, 28(4), pp. 701-712, (month unavailable) 1998, "Synthesis Of Novel Restricted Diamines; 2-(1-Aminocycloalkan-1-YL)Ethylamines" by T. Suzuki et al.

Justus Liebigs Ann. Chem., 661, (month unavailable) 19631 pp. 111-157, "Umsetzungen Mit Olefinen Und Aldehyden; Uber β-Lactame" by von Roderich Graf.

\* cited by examiner

HETARYL SUBSTITUTED HOMOTETRAMIC AND HOMOTETRONIC ACIDS AND THEIR USE THEREOF AS PESTICIDES

The present invention relates to new hetaryl-substituted homotetramic and homotetronic acids, to a plurality of processes for their preaparation, and to their use as pesticides, microbicides and herbicides.

It is known that certain tetrahydropyridones have herbicidal properties: JP-A-08-325230. Moreover, there are known specific 4-hydroxytetrahydropyridones which have acaricidal, insecticidal and herbicidal properties: JP-A-11 152 273.

However, the activity and range of action of these compounds is not always entirely satisfactory, in particular when low application rates and concentrations are used. Furthermore, these compounds are not always sufficiently well tolerated by plants.

It is furthermore known that certain 5,6-dihydropyrone derivatives, as protease inhibitors, have antiviral properties: WO 95/14012. Furthermore, 4-phenyl-6-(2-phenethyl)-5,6-dihydropyrone is known from the synthesis of kawalactone derivatives: Kappe et al.; Arch. Pharm. 309, 558–64, (1976). Moreover, 5,6-dihydropyrone derivatives are known as intermediates: White, J. D., Brenner, J. B., Deinsdale, M. J., J. Amer. Chem. Soc. 93, 281–2 (1971). Applications in crop protection have not been described as yet.

There have now been found new compounds of the formula (I)

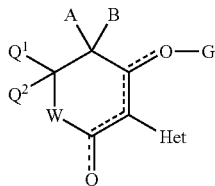

(I)

in which

Het represents a nitrogen-containing 5-membered heterocyclic ring which is substituted by halogen, alkyl, alkoxy, alkenyloxy, halogenoalkyl, halogenoalkoxy, halogenoalkenyloxy, cyano, nitro, alkylthio, alkylsulphinyl, alkylsulphonyl, optionally substituted phenyl or optionally substituted phenoxy, W represents oxygen or N-D, A represents hydrogen, in each case optionally halogen-substituted alkyl, alkenyl, alkoxyalkyl, polyalkoxyalkyl, alkylthioalkyl, saturated or unsaturated, optionally substituted cycloalkyl in which at least one ring atom is optionally replaced by a hetero atom, or represents aryl, arylalkyl or hetaryl, each of which is optionally substituted by halogen, alkyl, halogenoalkyl, alkoxy, halogenoalkoxy, cyano or nitro, B represents hydrogen or alkyl, or A and B together with the carbon atom to which they are bonded represent a saturated or unsaturated, unsubstituted or substituted cycle which optionally contains at least one hetero atom;

D represents hydrogen or an optionally substituted radical from the series comprising alkyl, alkenyl, alkinyl, alkoxyalkyl, polyalkoxyalkyl, alkylthioalkyl, saturated or unsaturated cycloalkyl in which one or more ring members are optionally replaced by hetero atoms, or arylalkyl, aryl, hetarylalkyl or hetaryl, or A and $Q^1$ together represent alkanediyl which is optionally substituted by in each case optionally substituted alkyl or alkoxy and in which two carbon atoms which are not directly adjacent optionally form a further optionally substituted cycle, or D and $Q^1$ together with the atoms to which they are bonded represent a saturated or unsaturated cycle which optionally contains at least one hetero atom and which is unsubstituted or substituted in the D, $Q^1$ moiety, $Q^1$ represents hydrogen, alkyl, alkoxyalkyl, optionally substituted cycloalkyl (in which one methylene group is optionally replaced by oxygen or sulphur) or optionally substituted phenyl, $Q^2$ represents hydrogen or alkyl, or $Q^1$ and $Q^2$ together with the carbon atom to which they are bonded represent an unsubstituted or substituted cycle which optionally contains one hetero atom, G represents hydrogen (a) or one of the groups

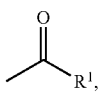

(b)

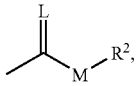

(c)

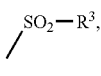

(d)

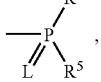

(e)

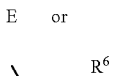

(f)

E or (g)

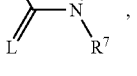

in which

E represents a metal ion or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or represents cycloalkyl which is optionally substituted by halogen, alkyl or alkoxy and which can be interrupted by at least one hetero atom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or in each case optionally substituted cycloalkyl, phenyl or benzyl, $R^3$ represents optionally alkyl, halogenoalkyl or optionally substituted phenyl or benzyl, $R^4$ and $R^5$ independently of one another represent in each case optionally halogen-substituted alkyl, alkoxy, alkylamino, dialkylamino, alkylthio, alkenylthio, cycloalkylthio and in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, optionally substituted phenyl, optionally substituted benzyl, or together with the N atom to which they are bonded represent a cycle which is optionally interrupted by oxygen or sulphur.

Depending on the nature of the substituents, the compounds of the formula (I) can exist as geometric and/or optical isomers or isomer mixtures of various compositions, and, if appropriate, these can be separated in the customary fashion. Not only the pure isomers, but also the isomer mixtures, their preparation and use and compositions comprising them are subject-matter of the present invention. However, the following text will, for the sake of simplicity, always mention compounds of the formula (I), even though this is understood as meaning not only the pure compounds, but also, if appropriate, mixtures with various amounts of isomeric compounds.

Depending on the position of the substituent G, the compounds of the formula (I) can exist in the two isomeric forms of the formulae (I-A) and (I-B), (I-A)

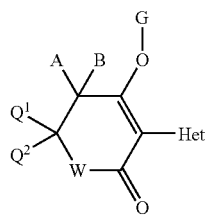

(I-B)

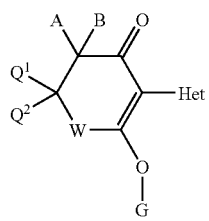

which is expressed by the broken line in formula (I).

The compounds of the formulae (I-A) and (I-B) can exist not only as mixtures, but also in the form of their pure isomers. If appropriate, mixtures of the compounds of the formulae (I-A) and (I-B) can be separated in a manner known per se by physical methods, for example by chromatographic methods.

The following text will only mention in each case one of the isomers which are possible, for the sake of clarity. This does not exclude that, if appropriate, the compounds may exist in the form of the isomer mixtures or in each case in the other isomeric form.

Taking into consideration the meanings thiazolyl for Het and oxygen and N-D for W, the following main structures (I-1) and (I-2) result (I-1)

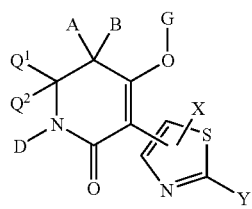

(I-2)

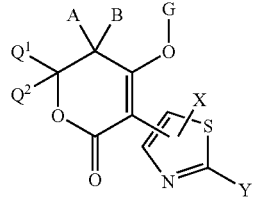

Taking into consideration the various meanings (a), (b), (c), (d), (e), (f) and (g) of group G, the following main structures (I-1-a) to (I-1-g) result if W is N-D (1), (I-1-a):

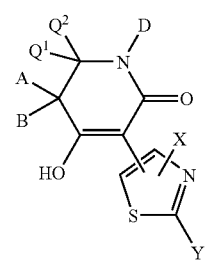

(I-1-b):

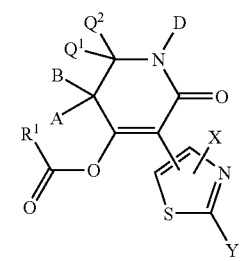

(I-1-c):

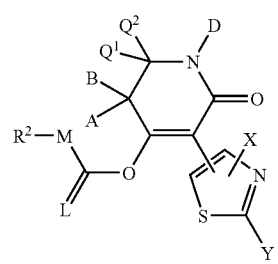

(I-1-d):

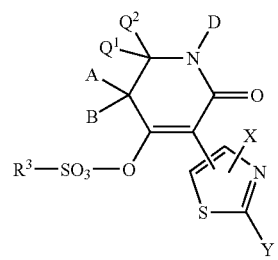

(I-1-e):

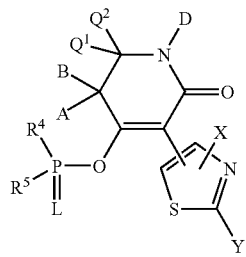

(I-1-f):

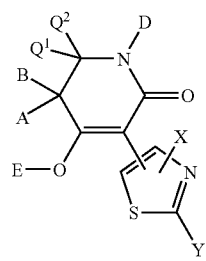

(I-1-g):

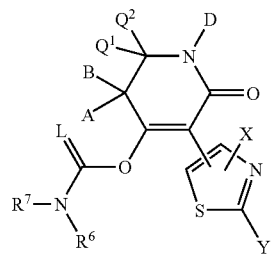

in which

A, B, D, E, L, M, $Q^1$, $Q^2$, $R^1$, $R^2$, $R^3$, $R^4$, $R^5$, $R^6$ and $R^7$ have the abovementioned meanings, X represents hydrogen, halogen, alkyl, alkoxy, alkenyloxy, nitro, cyano or optionally substituted phenyl and Y represents halogen, alkyl, halogenoalkyl, alkoxy, halogenoalkoxy, or in each case optionally substituted phenyl or phenoxy.

Taking into consideration the various meanings (a), (b), (c), (d), (e), (f) and (g) of group G, the following main structures (I-2-a) to (I-2-g) result if W is oxygen (2), (I-2-a):

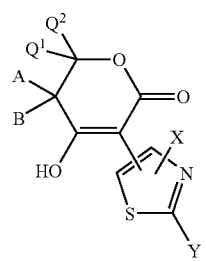

(I-2-b):

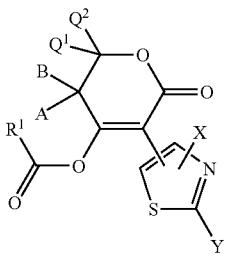

(I-2-c):

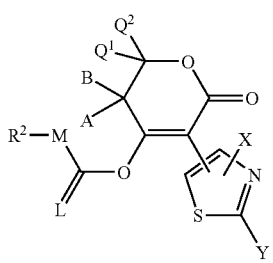

(I-2-d):

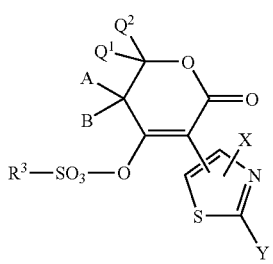

(I-2-e):

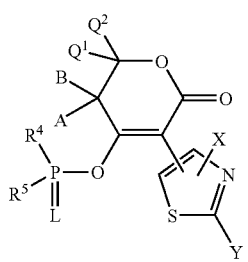

(I-2-f):

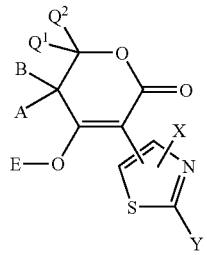

-continued (I-2-g):

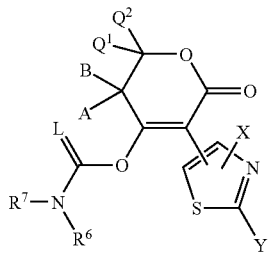

where

A, B, E, L, M, $Q^1$, $Q^2$, X, Y, $R^1$, $R^2$, $R^3$, $R^4$, $R^5$, $R^6$ and $R^7$ have the abovementioned meanings.

Furthermore, it has been found that the new compounds of the formula (I) are obtained by one of the processes described hereinbelow:

(A) Substituted tetrahydropyridine-2,4-diones or their enols of the formula (I-1-a)

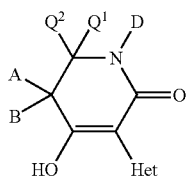

(I-1-a)

in which
A, B, D, $Q^1$, $Q^2$ and Het have the abovementioned meanings are obtained when
N-acylamino acid esters of the formula (II)

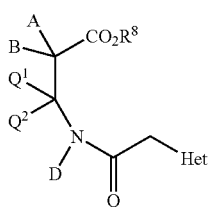

(II)

in which
A, B, D, $Q^1$, $Q^2$ and Het have the abovementioned meanings and
$R^8$ represents alkyl (preferably $C_1$–$C_6$-alkyl)
are subjected to an intramolecular condensation reaction in the presence of a diluent and in the presence of a base.

Furthermore, it has been found (B) that substituted 5,6-dihydropyrones of the formula (I-2-a)

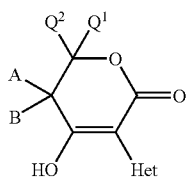

(I-2-a)

in which
A, B, $Q^1$, $Q^2$ and Het have the abovementioned meanings are obtained when
O-acylhydroxycarboxylic esters of the formula (III)

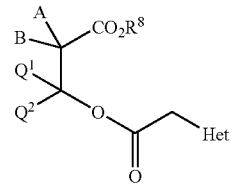

(III)

in which
A, B, $Q^1$, $Q^2$ and Het have the abovementioned meanings, and
$R^8$ represents alkyl (preferably $C_1$–$C_6$-alkyl)
are subjected to an intramolecular condensation reaction in the presence of a diluent and in the presence of a base.

Furthermore, it has been found, (C) that the compounds of the formulae (I-1-b) to (I-2-b) shown above in which A, B, $Q^1$, $Q^2$, $R^1$, W and Het have the abovementioned meanings are obtained when compounds of the formulae (I-1-a) to (I-2-a) shown above in which A, B, $Q^1$, $Q^2$, W and Het have the abovementioned meanings are reacted in each case (α) with acid halides of the formula (IV)

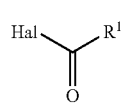

(IV)

in which
$R^1$ has the abovementioned meaning and
Hal represents halogen (in particular chlorine or bromine) or (β) with carboxylic anhydrides of the formula (V)

$$R^1\text{—CO—O—CO—}R^1 \quad (V)$$

in which
$R^1$ has the abovementioned meaning,
if appropriate in the presence of a diluent and if appropriate in the presence of an acid binder;

(D) that the compounds of the formulae (I-1-c) to (I-2-c) shown above in which A, B, $Q^1$, $Q^2$, $R^2$, M, W and Het have the abovementioned meanings and L represents oxygen are obtained when compounds of the formulae (I-1-a) to (I-2-a) shown above in which A, B, $Q^1$, $Q^2$, W and Het have the abovementioned meanings are reacted in each case
with chloroformic esters or chloroformic thioesters of the formula (VI)

$$R^2\text{-M-CO—Cl} \quad (VI)$$

in which
$R^2$ and M have the abovementioned meaning,
if appropriate in the presence of a diluent and if appropriate in the presence of an acid binder;

(E) that the compounds of the formulae (I-1-c) to (I-2-c) shown above in which A, B, $Q^1$, $Q^2$, $R^2$, M, W and Het have the abovementioned meanings and L represents sulphur are obtained when compounds of the formulae (I-1-a) to (I-2-a) shown above in which A, B, $Q^1$, $Q^2$, W and Het have the abovementioned meanings are reacted in each case
with chloromonothioformic esters or chlorodithioformic esters of the formula (VII)

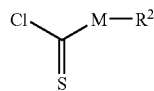 (VII)

in which
M and $R^2$ have the abovementioned meanings,
if appropriate in the presence of a diluent and if appropriate in the presence of an acid binder,
and
(F) that compounds of the formulae (I-1-d) to (I-2-d) shown above in which A, B, $Q^1$, $Q^2$, $R^3$, W and Het have the abovementioned meanings are obtained when compounds of the formulae (I-1-a) and (I-2-a) shown above in which A, B, $Q^1$, $Q^2$, W and Het have the abovementioned meanings are reacted in each case
with sulphonyl chlorides of the formula (VIII)

 (VIII)

in which:
$R^3$ has the abovementioned meaning,
if appropriate in the presence of a diluent and if appropriate in the presence of an acid binder,
(G) that compounds of the formulae (I-1-e) to (I-2-e) shown above in which A, B, L, $Q^1$, $Q^2$, $R^4$, $R^5$, W and Het have the abovementioned meanings are obtained when compounds of the formulae (I-1-a) to (I-2-a) shown above in which A, B, $Q^1$, $Q^2$, W and Het have the abovementioned meanings are reacted in each case
with phosphorus compounds of the formula (IX)

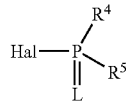 (IX)

in which
L, $R^4$ and $R^5$ have the abovementioned meanings and
Hal represents halogen (in particular chlorine or bromine),
if appropriate in the presence of a diluent and if appropriate in the presence of an acid binder,
(H) that compounds of the formulae (I-1-f) to (I-2-f) shown above in which A, B, E, $Q^1$, $Q^2$, W and Het have the abovementioned meanings are obtained when compounds of the formulae (I-1-a) to (I-2-a) in which A, B, $Q^1$, $Q^2$, W and Het have the abovementioned meanings are reacted in each case
with metal compounds or amines of the formula (X) or (XI)

 (X)

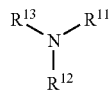 (XI)

in which
Me represents a monovalent or divalent metal (preferably an alkali metal or alkaline earth metal such as lithium, sodium, potassium, magnesium or calcium),
t represents the number 1 or 2 and
$R^{11}$, $R^{12}$, $R^{13}$ independently of one another represent hydrogen or alkyl (preferably $C_1$–$C_8$-alkyl)
are reacted, if appropriate in the presence of a diluent,
(I) that compounds of the formulae (I-1-g) to (I-2-g) shown above in which A, B, L, $Q^1$, $Q^2$, $R^6$, $R^7$, W and Het have the abovementioned meanings are obtained when compounds of the formulae (I-1-a) to (I-2-a) shown above in which A, B, $Q^1$, $Q^2$, W and Het have the abovementioned meanings are reacted in each case
(α) with isocyanates or isothiocyanates of the formula (XII)

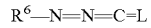 (XII)

in which
$R^6$ and L have the abovementioned meanings,
if appropriate in the presence of a diluent and if appropriate in the presence of a catalyst, or
(β) with carbamoyl chlorides or thiocarbamoyl chlorides of the formula (XIII)

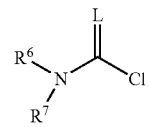 (XIII)

in which
L, $R^6$ and $R^7$ have the abovementioned meanings,
if appropriate in the presence of a diluent and if appropriate in the presence of acid binder.

Furthermore, it has been found that the new compounds of the formula (I) have very good activity as pesticides, preferably as insecticides, acaricides and also herbicides.

Formula (I) provides a general definition of the compounds according to the invention. Preferred substituents or ranges of the radicals stated in the formulae mentioned hereinabove and hereinbelow are illustrated in the following text:

Het preferably represents

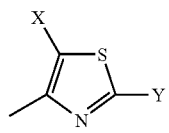

W preferably represents oxygen or N-D,
X preferably represents hydrogen, halogen, $C_1$–$C_6$-alkyl, $C_1$–$C_6$-alkoxy, $C_3$–$C_6$-alkenyloxy, nitro, cyano, or represents phenyl which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano,
Y preferably represents halogen, $C_1$–$C_6$-alkyl, $C_1$–$C_6$-halogenoalkyl, $C_1$–$C_6$-alkoxy, $C_1$–$C_6$-halogenoalkoxy or the groups

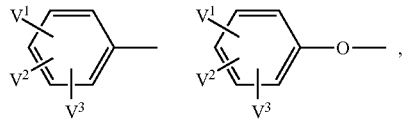

V¹ preferably represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-halogenoalkyl, $C_1$–$C_4$-halogenoalkoxy, nitro, cyano, or represents phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally monosubstituted or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro or cyano, V² and V³ preferably independently of one another represent hydrogen, halogen, $C_1$–$C_6$-alkyl, $C_1$–$C_6$-alkoxy, $C_1$–$C_4$-halogenoalkyl or $C_1$–$C_4$-halogenoalkoxy, V¹ and V² together with the carbon atoms to which they are bonded preferably represent a 5- or 6-membered cycle which is optionally substituted by $C_1$–$C_4$-alkyl or halogen and in which one to three carbon atoms can optionally be replaced by oxygen, sulphur or nitrogen, A preferably represents hydrogen, or represents $C_1$–$C_{12}$-alkyl, $C_3$–$C_8$-alkenyl, $C_1$–$C_6$-alkoxy-$C_1$–$C_4$-alkyl, each of which is optionally substituted by halogen, or represents optionally halogen-, $C_1$–$C_4$-alkyl- or $C_1$–$C_4$-alkoxy-substituted $C_3$–$C_8$-cycloalkyl or $C_3$–$C_6$-cycloalkyl-$C_1$–$C_4$-alkyl in which one or two ring members which are not directly adjacent are optionally replaced by oxygen and/or sulphur, or represents phenyl, benzyl, hetaryl having 5 to 6 ring atoms (for example furanyl, pyridyl, imidazolyl, triazolyl, pyrazolyl, pyrimidyl, thiazolyl or thienyl) or hetaryl-$C_1$–$C_4$-alkyl having 5 to 6 ring atoms (for example pyridyl, pyrimidyl or thiazolyl), each of these cycles optionally being substituted by halogen, $C_1$–$C_6$-alkyl, $C_1$–$C_6$-halogenoalkyl, $C_1$–$C_6$-alkoxy, $C_1$–$C_6$-halogenoalkoxy, cyano or nitro, B preferably represents hydrogen or $C_1$–$C_6$-alkyl, A, B and the carbon atom to which they are bonded preferably represent saturated $C_3$–$C_{10}$-cycloalkyl or unsaturated $C_5$–$C_{10}$-cycloalkyl in which one ring member is optionally replaced by oxygen or sulphur and which are optionally monosubstituted or disubstituted by $C_1$–$C_6$-alkyl, $C_3$–$C_8$-cycloalkyl, $C_1$–$C_6$-halogenoalkyl, $C_1$–$C_6$-alkoxy, $C_1$–$C_6$-alkylthio, halogen or phenyl, D preferably represents hydrogen, in each case optionally halogen-substituted $C_1$–$C_6$-alkyl, $C_3$–$C_8$-alkenyl, $C_3$–$C_8$-alkinyl, $C_1$–$C_6$-alkoxy-$C_2$–$C_6$-alkyl, or represents optionally halogen-, $C_1$–$C_4$-alkyl-, $C_1$–$C_4$-alkoxy- or $C_1$–$C_4$-halogenoalkyl-substituted $C_3$–$C_8$-cycloalkyl or $C_3$–$C_6$-cycloalkyl-$C_1$–$C_4$-alkyl in which one ring member is optionally replaced by oxygen or sulphur, A and Q¹ jointly preferably represent $C_3$–$C_6$-alkanediyl which is optionally substituted by $C_1$–$C_4$-alkyl or $C_1$–$C_4$-alkoxy, D and Q¹ together preferably represent $C_3$–$C_6$-alkanediyl which is optionally monosubstituted or disubstituted by identical or different substituents from the series consisting of $C_1$–$C_4$-alkyl and $C_1$–$C_4$-alkoxy, or Q¹ preferably represents hydrogen, $C_1$–$C_6$-alkyl, $C_1$–$C_6$-alkoxy-$C_1$–$C_2$-alkyl, or represents $C_3$–$C_8$-cycloalkyl in which one methylene group is optionally replaced by oxygen or sulphur and which is optionally substituted by fluorine, chlorine, $C_1$–$C_4$-alkyl, $C_1$–$C_2$-halogenoalkyl or $C_1$–$C_4$-alkoxy, or represents phenyl which is optionally substituted by halogen, $C_1$–$C_4$-alkyl, $C_1$–$C_4$-alkoxy, $C_1$–$C_2$-halogenoalkyl, $C_1$–$C_2$-halogenoalkoxy, cyano or nitro, Q² preferably represents hydrogen or $C_1$–$C_4$-alkyl, Q¹ and Q² preferably together with the carbon atom to which they are bonded represent $C_3$–$C_7$-cycloalkyl in which one ring member is optionally replaced by oxygen or sulphur and which is optionally substituted by $C_1$–$C_6$-alkyl, $C_1$–$C_6$-alkoxy or $C_1$–$C_2$-halogenoalkyl, G preferably represents hydrogen (a) or one of the groups

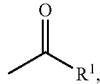

(b)

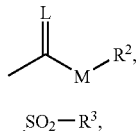

(c)

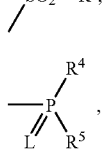

(d)

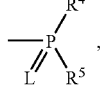

(e)

E (f) or

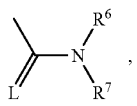

(g)

(g), in particular (a), (b), (c) or (g), in which

E represents a metal ion or an ammonium ion,

L represents oxygen or sulphur and

M represents oxygen or sulphur,

R¹ preferably represents $C_1$–$C_{20}$-alkyl, $C_2$–$C_{20}$-alkenyl, $C_1$–$C_8$-alkoxy-$C_{1-C8}$-alkyl, $C_1$–$C_8$-alkylthio-$C_1$–$C_8$-alkyl, poly-$C_1$–$C_8$-alkoxy-$C_1$–$C_8$-alkyl, each of which is optionally substituted by halogen, or represents $C_3$–$C_8$-cycloalkyl in which one or more (preferably one or two) ring members which are not directly adjacent are optionally replaced by oxygen and/or sulphur and which is optionally substituted by halogen, $C_1$–$C_6$-alkyl or $C_1$–$C_6$-alkoxy, or represents phenyl which is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulphonyl, or represents phenyl-$C_1$–$C_6$-alkyl which is optionally substituted by halogen, nitro, cyano, $C_1$–$C_6$-alkyl, $C_1$–$C_6$-alkoxy, $C_1$–$C_6$-halogenoalkyl or $C_1$–$C_6$-halogenoalkoxy, or represents 5- or 6-membered hetaryl (for example pyrazolyl, thiazolyl, pyridyl, pyrimidyl, furanyl or thienyl) which is optionally substituted by halogen, $C_1$–$C_6$-alkyl or trifluoromethyl, or represents phenoxy-$C_1$–$C_6$-alkyl which is optionally substituted by halogen or $C_1$–$C_6$-alkyl, or represents 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl), which is optionally substituted by halogen, amino or $C_1$–$C_6$-alkyl, R² preferably represents $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, each of which is optionally substituted by halogen, or represents $C_3$–$C_8$-cycloalkyl which is optionally substituted by halogen, $C_1$–$C_6$-alkyl or $C_1$–$C_6$-alkoxy, or represents phenyl or benzyl, each of which is optionally substituted by halogen, cyano, nitro, $C_1$–$C_6$-alkyl, $C_1$–$C_6$-alkoxy, $C_1$–$C_6$-halogenoalkyl or $C_1$–$C_6$-halogenalkoxy, $R^3$ preferably represents $C_1$–$C_8$-alkyl which is optionally substituted by halogen or represents phenyl or benzyl, each of which is optionally substituted by halogen, $C_1$–$C_6$-alkyl, $C_1$–$C_6$-alkoxy, $C_1$–$C_4$-halogenoalkyl, $C_1$–$C_4$-halogenoalkoxy, cyano or nitro, $R^4$ and $R^5$ preferably independently of one another represent $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio, each of which is optionally substituted by halogen, or represent phenyl, benzyl, phenoxy or phenylthio, each of which is optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another preferably represent hydrogen, or represent $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, each of which is optionally substituted by halogen, or represent phenyl which is optionally substituted by halogen, $C_1$–$C_8$-halogenoalkyl, $C_1$–$C_8$-alkyl or $C_1$–$C_8$-alkoxy, or represent benzyl which is optionally substituted by halogen, $C_1$–$C_8$-alkyl, $C_1$–$C_8$-halogenoalkyl or $C_1$–$C_8$-alkoxy, or together with the N atom to which they are bonded represent a $C_3$–$C_6$-alkylene radical in which one carbon atom is optionally replaced by oxygen or sulphur and which is optionally substituted by $C_1$–$C_4$-alkyl.

In the definitions of radicals mentioned as being preferred, halogen, also as a substituent such as, for example, in halogenoalkyl, represents fluorine, chlorine, bromine and iodine, in particular fluorine or chlorine.

Het especially preferably represents

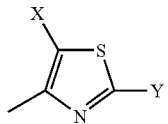

W especially preferably represents oxygen or N-D,

X especially preferably represents hydrogen, chlorine, bromine, $C_1$–$C_4$-alkyl, or represents phenyl which is optionally monosubstituted to disubstituted by fluorine, chlorine, bromine, $C_1$–$C_4$-alkyl, $C_1$–$C_2$-halogenoalkoxy, nitro or cyano, Y especially preferably represents chlorine, bromine, $C_1$–$C_4$-alkyl, $C_1$–$C_4$-halogenoalkyl, $C_1$–$C_4$-alkoxy, $C_1$–$C_4$-halogenoalkoxy or the groups

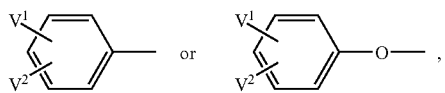

$V^1$ especially preferably represents hydrogen, fluorine, chlorine, bromine, $C_1$–$C_6$-alkyl, $C_1$–$C_4$-alkoxy, $C_1$–$C_2$-halogenoalkyl, $C_1$–$C_2$-halogenalkoxy, nitro, cyano, or represents phenyl, phenoxy, phenoxy-$C_1$–$C_2$-alkyl, phenyl-$C_1$–$C_2$-alkoxy, phenylthio-$C_1$–$C_2$-alkyl or phenyl-$C_1$–$C_2$-alkylthio, each of which is optionally monosubstituted or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenoalkoxy, nitro or cyano $V^2$ especially preferably represents hydrogen, fluorine, chlorine, bromine, $C_1$–$C_4$-alkyl, $C_1$–$C_4$-alkoxy, $C_1$–$C_2$-halogenoalkyl or $C_1$–$C_2$-halogenoalkoxy, $V^1$ and $V^2$ jointly together with the carbon atoms to which they are bonded especially preferably represent a 5- or 6-membered cycle in which one or two carbon atoms can optionally be replaced by oxygen and which is optionally substituted by fluorine or methyl, A especially preferably represents hydrogen, or represents $C_1$–$C_8$-alkyl or $C_1$–$C_4$-alkoxy-$C_1$–$C_2$-alkyl, each of which is optionally substituted by fluorine, or represents $C_5$–$C_6$-cycloalkyl or $C_3$–$C_6$-cycloalkyl-$C_1$–$C_2$-alkyl in which one ring member is optionally replaced by oxygen or sulphur and which is optionally substituted by fluorine, chlorine, methyl, ethyl or methoxy, or represents phenyl or benzyl, each of which is optionally substituted by fluorine, chlorine, bromine, $C_1$–$C_4$-alkyl, $C_1$–$C_2$-halogenoalkyl, $C_1$–$C_4$-alkoxy or $C_1$–$C_2$-halogenoalkoxy, B especially preferably represents hydrogen or $C_1$–$C_4$-alkyl, A, B and the carbon atom to which they are bonded especially preferably represent saturated $C_5$–$C_7$-cycloalkyl in which one ring member is optionally replaced by oxygen and which is optionally monosubstituted by $C_1$–$C_4$-alkyl, trifluoromethyl or $C_1$–$C_4$-alkoxy, D especially preferably represents hydrogen, or represents $C_1$–$C_6$-alkyl, $C_3$–$C_6$-alkenyl or $C_1$–$C_4$-alkoxy-$C_2$–$C_3$-alkyl, each of which is optionally substituted by fluorine, or represents $C_3$–$C_7$-cycloalkyl or $C_3$–$C_6$-cycloalkyl-$C_1$–$C_2$-alkyl in which one methylene group is optionally replaced by oxygen and which is optionally substituted by $C_1$–$C_2$-alkyl, fluorine or chlorine, A and $Q^1$ jointly especially preferably represent $C_3$–$C_4$-alkanediyl, D and $Q^1$ jointly especially preferably represent $C_3$–$C_4$-alkanediyl, $Q^1$ especially preferably represents hydrogen, $C_1$–$C_4$-alkyl, $C_1$–$C_4$-alkoxy-$C_1$–$C_2$-alkyl, or represents $C_3$–$C_6$-cycloalkyl in which one methylene group is optionally replaced by oxygen and which is optionally substituted by methyl or methoxy, $Q^2$ especially preferably represents hydrogen, methyl or ethyl, $Q^1$ and $Q^2$ especially preferably jointly with the carbon atom to which they are bonded represent saturated $C_5$–$C_6$-cycloalkyl in which one ring member is optionally replaced by oxygen and which is optionally substituted by $C_1$–$C_4$-alkyl or $C_1$–$C_4$-alkoxy, G especially preferably represents hydrogen (a) or one of the groups

(b)

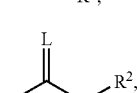
(c)

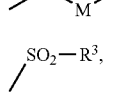
(d)

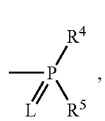
(e)

E (f) or

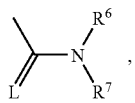
(g), (g), in particular (a), (b), (c) or (g),
in which
E represents a metal ion or an ammonium ion,
L represents oxygen or sulphur and
M represents oxygen or sulphur, $R^1$ especially preferably represents $C_1$–$C_{16}$-alkyl, $C_2$–$C_{16}$-alkenyl, $C_1$–$C_4$-alkoxy-$C_1$–$C_2$-alkyl, $C_1$–$C_4$-alkylthio-$C_1$–$C_2$-alkyl, each of which is optionally substituted by fluorine or chlorine, or represents $C_3$–$C_7$-cycloalkyl in which one or two ring members which are not directly adjacent are optionally replaced by oxygen and/or sulphur and which is optionally substituted by fluorine, chlorine, $C_1$–$C_5$-alkyl or $C_1$–$C_5$-alkoxy,
    or represents phenyl which is optionally substituted by fluorine, chlorine, bromine, cyano, nitro, $C_1$–$C_4$-alkyl, $C_1$–$C_4$-alkoxy, trifluoromethyl or trifluoromethoxy;
    or represents pyridyl or thienyl, each of which is optionally substituted by fluorine, chlorine, bromine, methyl, ethyl or trifluoromethyl, $R^2$ especially preferably represents $C_1$–$C_{16}$-alkyl, $C_2$–$C_{16}$-alkenyl or $C_1$–$C_4$-alkoxy-$C_2$–$C_4$-alkyl, each of which is optionally substituted by fluorine,
    or represents $C_3$–$C_7$-cycloalkyl which is optionally, substituted by methyl, ethyl or methoxy,
    or represents phenyl or benzyl, each of which is optionally substituted by fluorine, chlorine, bromine, cyano, nitro, $C_1$–$C_4$-alkyl, $C_1$–$C_3$-alkoxy, trifluoromethyl or trifluoromethoxy, $R^3$ especially preferably represents $C_1$–$C_6$-alkyl which is optionally substituted by fluorine, or represents phenyl which is substituted by fluorine, chlorine, bromine, $C_1$–$C_4$-alkyl, $C_1$–$C_4$-alkoxy, trifluoromethyl, trifluoromethoxy, cyano or nitro, $R^4$ especially preferably represents $C_1$–$C_6$-alkyl, $C_1$–$C_6$-alkoxy, $C_1$–$C_6$-alkyl amino, di-($C_1$–$C_6$-alkyl)amino, $C_1$–$C_6$-alkylthio, or represents phenyl, benzyl, phenoxy or phenylthio, each of which is optionally substituted by fluorine, chlorine, bromine, nitro, cyano, $C_1$–$C_3$-alkoxy, trifluoromethoxy, $C_1$–$C_3$-alkyl or trifluoromethyl, $R^5$ especially preferably represents $C_1$–$C_4$-alkyl, $C_1$–$C_4$-alkoxy or $C_1$–$C_4$-alkylthio, $R^6$ especially preferably represents hydrogen, $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, or represents phenyl which is optionally substituted by fluorine, chlorine, bromine, trifluoromethyl, $C_1$–$C_4$-alkyl or $C_1$–$C_4$-alkoxy, or represents benzyl which is optionally substituted by fluorine, chlorine, bromine, methyl, ethyl, trifluoromethyl or methoxy, $R^7$ especially preferably represents hydrogen, $C_1$–$C_6$-alkyl or $C_3$–$C_6$-alkenyl, $R^6$ and $R^7$ especially preferably together with the N atom to which they are bonded represent a $C_4$–$C_6$-alkylene radical in which one methylene group is optionally replaced by oxygen or sulphur and which is optionally substituted by methyl or ethyl.

In the definitions of radicals which have been mentioned as being especially preferred, halogen, also as substituent such as, for example, in halogenoalkyl, represents fluorine, chlorine, bromine and iodine, especially fluorine and chlorine, very especially fluorine.

Het very especially preferably represents

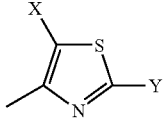

W very especially preferably represents oxygen or N-D,

X very especially preferably represents chlorine, bromine, methyl, ethyl, n-propyl, isopropyl, n-butyl or isobutyl, Y very especially preferably represents methyl, ethyl, n-propyl, isopropyl, n-butyl, isobutyl, tert-butyl or the group

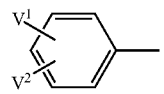

$V^1$ very especially preferably represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, trifluoromethoxy, $V^2$ very especially preferably represents hydrogen, fluorine, chlorine, methyl, ethyl, n-propyl, isopropyl, methoxy, ethoxy, trifluoromethyl or trifluoromethoxy, A very especially preferably represents hydrogen, methyl, ethyl, propyl, isopropyl, butyl, isobutyl, methoxymethyl, ethoxymethyl, B very especially preferably represents hydrogen, methyl or ethyl, A, B and the carbon atom to which they are bonded very especially preferably represent saturated $C_5$–$C_6$-cycloalkyl in which one ring member is optionally replaced by oxygen and which is optionally monosubstituted by methyl, ethyl, n-propyl, isopropyl, butyl, trifluoromethyl, methoxy, ethoxy, n-propoxy or n-butoxy, D very especially preferably represents hydrogen, methyl, ethyl, propyl, isopropyl, allyl, 2-butenyl, methoxyethyl, ethoxyethyl, cyclopropyl, cyclopentyl or cyclohexyl, A and $Q^1$ jointly very especially preferably represent $C_3$–$C_4$-alkanediyl.

D and $Q^1$ jointly very especially preferably represent $C_3$–$C_4$-alkanediyl, $Q^1$ very especially preferably represents hydrogen, methyl, ethyl, propyl, isopropyl, cyclopropyl, cyclopentyl or cyclohexyl, $Q^2$ very especially preferably represents hydrogen, methyl or ethyl, $Q^1$ and $Q^2$ very especially preferably jointly with the carbon to which they are bonded represent saturated $C_5$–$C_6$-cycloalkyl in which one ring member is optionally replaced by oxygen and which is optionally substituted by methyl, ethyl, propyl, isopropyl, methoxy, ethoxy, propoxy or butoxy, G very especially preferably represents hydrogen (a) or one of the groups

(b)

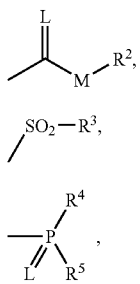
(c)

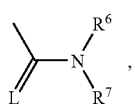
(d)

(e)

E (f) or (g)

(g), in particular (a), (b), (c) or (g),
in which
E represents a metal ion or an ammonium ion,
L represents oxygen or sulphur and
M represents oxygen or sulphur, $R^1$ very especially preferably represents $C_1$–$C_4$-alkyl, $C_2$–$C_{14}$-alkenyl, $C_1$–$C_4$-alkoxy-$C_1$–$C_2$-alkyl, $C_1$–$C_4$-alkylthio-$C_1$–$C_2$-alkyl, each of which is optionally substituted by fluorine or chlorine, or represents $C_3$–$C_6$-cycloalkyl in which one or two ring members which are not directly adjacent are optionally replaced by oxygen and/or sulphur and which is optionally substituted by fluorine, chlorine, methyl, ethyl or methoxy, or represents phenyl which is optionally substituted by fluorine, chlorine, bromine, cyano, nitro, methyl, ethyl, isopropyl, tert-butyl, methoxy, trifluoromethyl or trifluoromethoxy, or represents thienyl or pyridyl, each of which is optionally substituted by fluorine, chlorine, bromine or methyl, $R^2$ very especially preferably represents $C_1$–$C_{14}$-alkyl, $C_2$–$C_{14}$-alkenyl or $C_1$–$C_4$-alkoxy-$C_2$–$C_3$-alkyl, each of which is optionally substituted by fluorine, or represents $C_3$–$C_6$-cycloalkyl which is optionally substituted by methyl, ethyl or methoxy, or represents phenyl or benzyl, each of which is optionally substituted by fluorine, chlorine, cyano, nitro, methyl, ethyl, isopropyl, tert-butyl, methoxy, trifluoromethyl or trifluoromethoxy, $R^3$ very especially preferably represents methyl, ethyl, n-propyl, isopropyl, each of which is optionally substituted by fluorine, or represents phenyl which is optionally substituted by fluorine, chlorine, bromine, methyl, tert-butyl, methoxy, trifluoromethyl, trifluoromethoxy, cyano or nitro, $R^4$ very especially preferably represents $C_1$–$C_4$-alkyl, $C_1$–$C_4$-alkoxy, $C_1$–$C_4$-alkylamino, di-($C_1$–$C_4$-alkyl) amino, $C_1$–$C_4$-alkylthio or represents phenyl, phenoxy or phenylthio, each of which is optionally substituted by fluorine, chlorine, bromine, nitro, cyano, $C_1$–$C_2$-alkoxy, trifluoromethoxy or $C_1$–$C_3$-alkyl, $R^5$ very especially preferably represents methyl, ethyl, methoxy, ethoxy, methylthio or ethylthio, $R^6$ and $R^7$ independently of one another very especially preferably represent hydrogen, $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl, $R^7$ very especially preferably represents hydrogen, $C_1$–$C_4$-alkyl or $C_3$–$C_4$-alkenyl, $R^6$ and $R^7$ very especially preferably together with the N atom to which they are bonded represent a $C_5$–$C_6$-alkylene radical in which one methylene group is optionally replaced by oxygen or sulphur.

Het most especially preferably represents

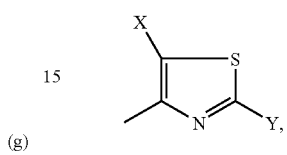

W most especially preferably represents oxygen or N-D,
X most especially preferably represents chlorine, methyl, ethyl, n-propyl or i-propyl,
Y most especially preferably represents

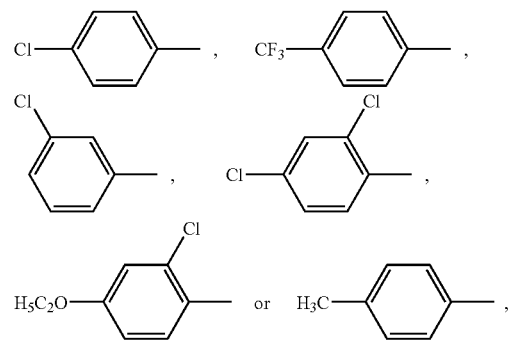

A most especially preferably represents hydrogen or methyl,
B most especially preferably represents hydrogen or methyl,
A, B and the carbon atom to which they are bonded most especially preferably represent saturated $C_6$-cycloalkyl in which one ring member is optionally replaced by oxygen,
D most especially preferably represents hydrogen or cyclopropyl,
D and $Q^1$ most especially preferably jointly represent $C_3$–$C_4$-alkanediyl,
$Q^1$ most especially preferably represents methyl or hydrogen,
$Q^2$ most especially preferably represents methyl or hydrogen,
$Q^1$ and $Q^2$ most especially preferably jointly with the carbon to which they are bonded represent saturated $C_6$-cycloalkyl in which one ring member is optionally replaced by oxygen,
G most especially preferably represents hydrogen (a) or one of the groups (b)

(c)

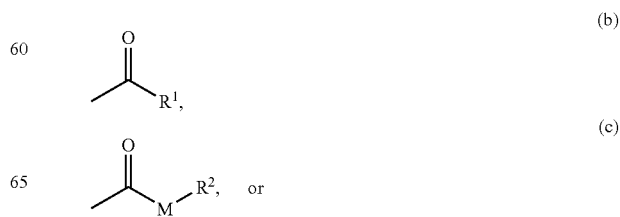

-continued

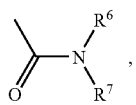
(g)

where M represents oxygen or sulphur,

R$^1$ most especially preferably represents C$_1$–C$_4$-alkyl, C$_1$–C$_4$-alkoxy-C$_1$–C$_2$-alkyl, or represents phenyl or pyridyl, each of which is optionally substituted by chlorine, R$^2$ most especially preferably represents C$_1$–C$_4$-alkyl, phenyl or benzyl, R$^6$ and R$^7$ most especially preferably together with the N atom to which they are bonded represent a C$_5$–C$_6$-alkylene radical in which one methylene group is optionally replaced by oxygen.

The definitions or explanations stated above in general or in preferred ranges can be combined with each other as desired, that is to say combinations between the respective ranges and preferred ranges are also possible. They apply to the end products and, analogously, to the precursors and intermediates.

Preferred in accordance with the invention are the compounds of the formula (I) with a combination of the meanings stated above as being preferred (given preference to).

Especially preferred in accordance with the invention are the compounds of the formula (I) with a combination of the meanings stated above as especially preferred.

Very especially preferred in accordance with the invention are the compounds of the formula (I) with a combination of the meanings stated above as very especially preferred.

Most especially preferred in accordance with the invention are the compounds of the formula (I) with a combination of the meanings stated above as most preferred.

Particularly preferred are compounds of the formula (I) in which G is hydrogen.

Further compounds of the formula (I) which are particularly preferred are those in which D represents hydrogen, methyl, ethyl, propyl, isopropyl, cyclopropyl, cyclopentyl or cyclohexyl.

Saturated or unsaturated hydrocarbon radicals such as alkyl or alkenyl, also in connection with hetero atoms such as, for example, in alkoxy, can be in each case straight-chain or branched as far as this is possible.

Unless otherwise defined, optionally substituted radicals can be monosubstituted or polysubstituted, it being possible for the substituents to be identical or different in the case of polysubstitutions.

If, in accordance with process (A), ethyl N-[4-(5-methyl)-2-(4-chlorophenyl)-thiazolylacetyl]-1-aminomethyl-cyclohexane-carboxylate is used as starting material, the course of the process according to the invention can be represented by the following equation:

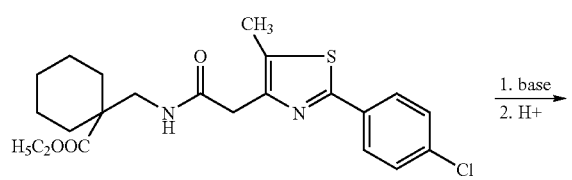

If, in accordance with process (B), ethyl O-[4-(5-methyl)-2-(4-chlorophenyl)-thiazolylacetyl]-1-hydroxymethyl-cyclohexane-carboxylate is used as starting material, the course of the process according to the invention can be represented by the following equation:

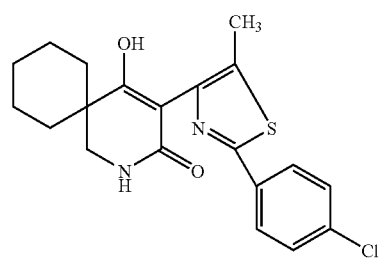

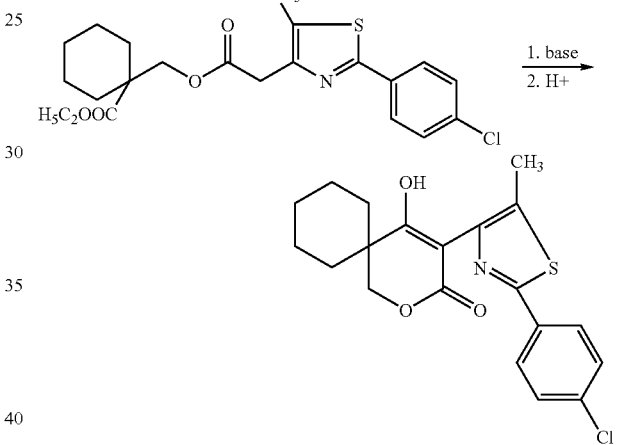

If, in accordance with process (Dα), 3-[4-(5-methyl-2-(3-chlorophenyl)-thiazolyl]-4-hydroxy-6,6-dimethyldihydropyridin-2-one and pivaloyl chloride are used as starting materials, the course of the process according to the invention can be represented by the following equation:

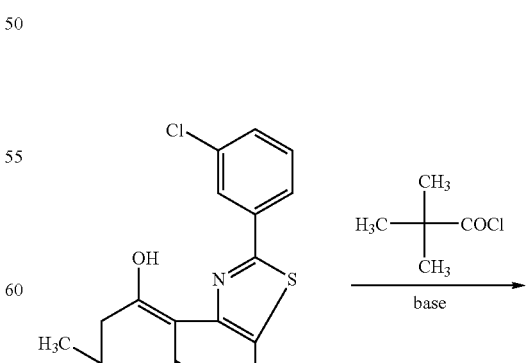

-continued

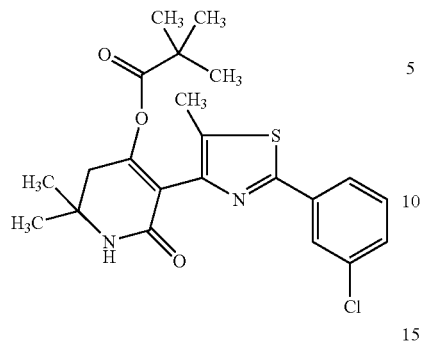

If, in accordance with process (Dβ), 3-[4-(5-ethyl-2-(4-methoxyphenyl))-thiazolyl]-4-hydroxy-6,6-dimethyldihydropyrone and acetic anhydride are used as starting materials, the course of the process according to the invention can be represented by the following equation:

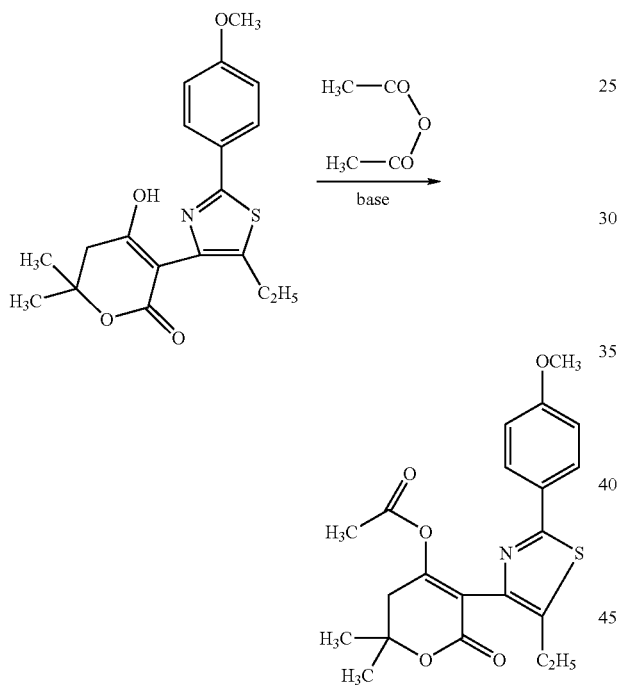

If, in accordance with process (E), 3-[4-(5-methyl-2-phenyl)-thiazolyl]-6,6-dimethyldihydropyridine-2,4-dione and ethoxyethyl chloroformate are used as starting compounds, the course of the process according to the invention can be represented by the following equation:

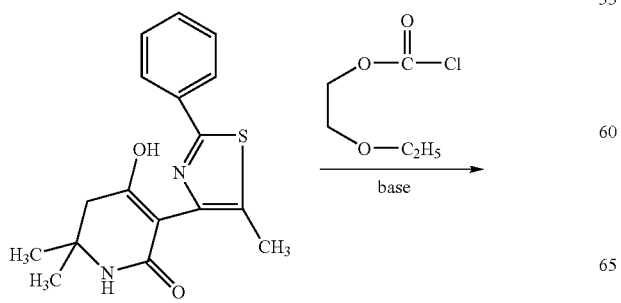

-continued

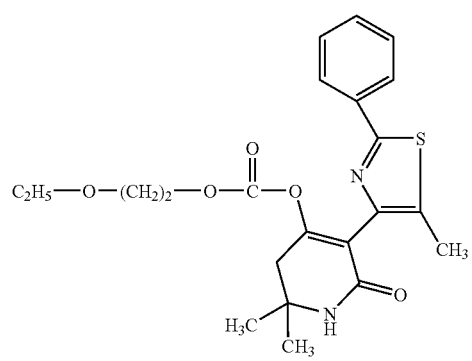

If, in accordance with process (F), 3-[4-(5-methyl-2-(4-fluorophenyl))-thiazolyl]-5,5,6,6-tetramethyldihydropyrone and methyl chloromonothioformate are used as starting materials, the course of the reaction can be represented as follows:

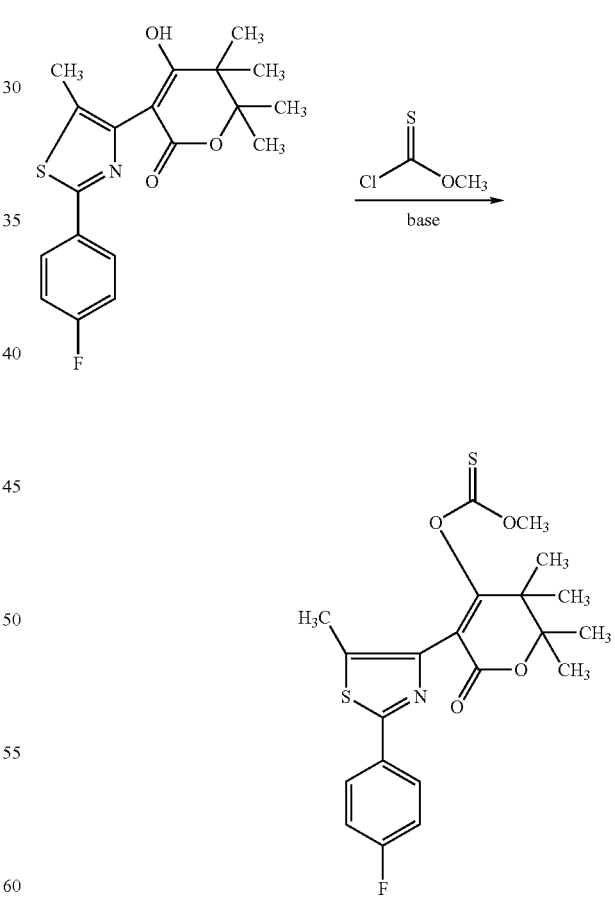

If, in accordance with process (G), 3-[4-(5-methyl-3-(4-methylphenyl)-thiazolyl]-6,6-dimethyldihydropyridine-2,4-dione and methanesulphonyl chloride are used as starting materials, the course of the reaction can be represented by the following equation:

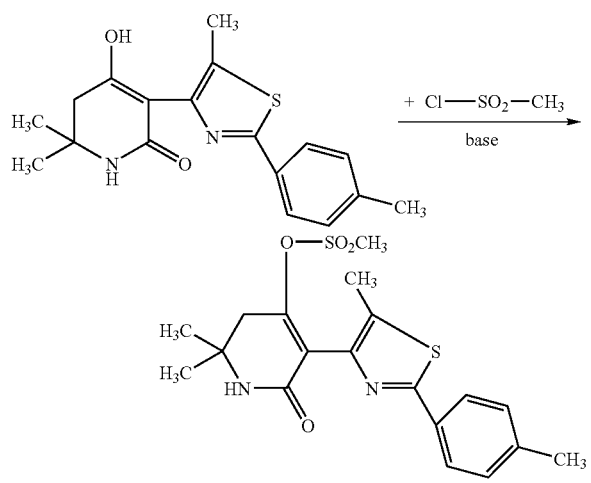

If, in accordance with process (H), 3-[4-(5-methyl-2-phenyl)-thiazolyl]-4-hydroxy-5,5,6,6-tetramethyldihydropyrone and methanethio-phosphonyl chloride 2,2,2-trifluoroethyl ester are used as starting materials, the course of the reaction can be represented by the following equation:

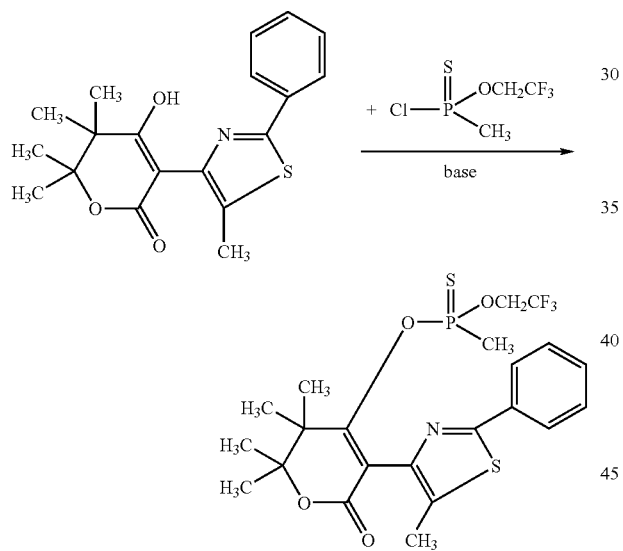

If, in accordance with process (I,) 3-[4-(5-methyl-2-(4-trifluoromethylphenyl))-thiazolyl]-6,6-dimethyl-dihydropyridine-2,4-dione and NaOH are used as reactants, the course of the process according to the invention can be represented by the following equation:

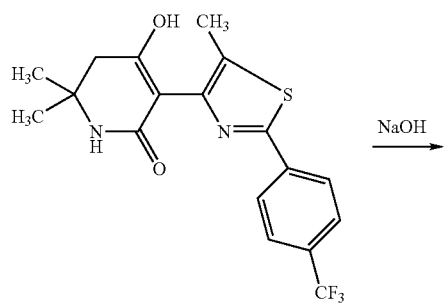

-continued

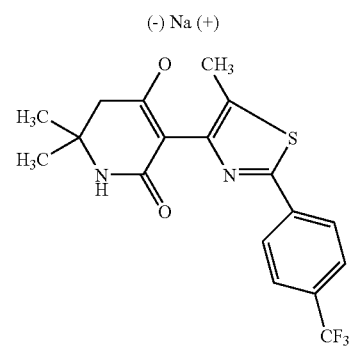

If, in accordance with process (Jα), 3-[4-(5-methyl-2-(3-trifluoromethylphenyl))-thiazolyl]-4-hydroxy-5,5,6,6-tetramethyldihydropyrone and ethyl isocyanate are used as starting materials, the course of the reaction can be represented by the following equation:

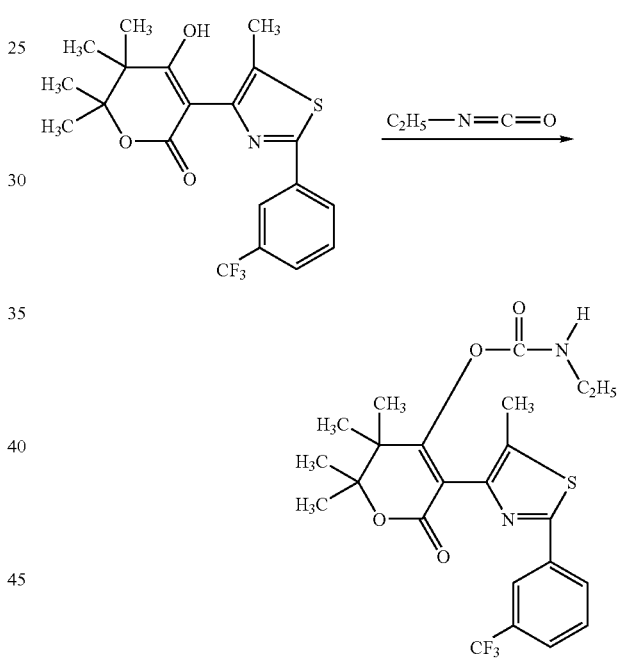

If, in accordance with process (Jβ), 3-[4-(5-methyl-2-phenyl)-thiazolyl]-6,6-dimethyl-dihydropyridine-2,4-dione and dimethylcarbamoyl chloride are used as starting materials, the course of the reaction can be represented by the following scheme:

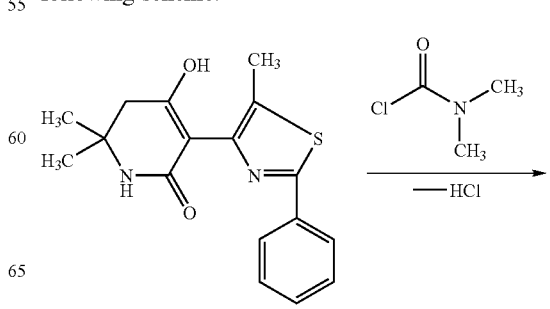

-continued

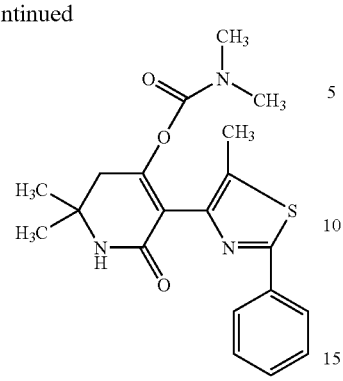

The compounds of the formula (II)

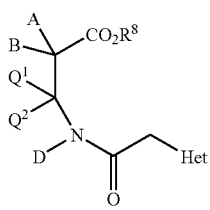
(II)

in which

A, B, D, $Q^1$, $Q^2$, Het and $R^8$ have the abovementioned meanings and which are required as starting materials in process (A) according to the invention are new.

The acylamino acid esters of the formula (II) are obtained, for example, from amino acid derivatives of the formula (XIV)

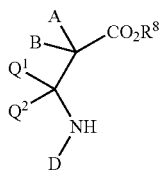
(XIV)

in which

A, B, $Q^1$, $Q^2$, $R^8$ and D have the abovementioned meanings are acylated with substituted hetaryl acetic acid derivatives of the formula (XV)

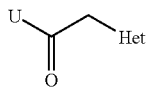
(XV)

in which

Het has the abovementioned meaning and

U represents a leaving group introduced by reagents for the activation of carboxylic acids, such as carbonyldiimidazole, carbonyldiimide (such as, for example, dicyclohexylcarbodiimide), phosphorylating agents (such as, for example, POCl$_3$, BOP-Cl), halogenating agents, for example thionyl chloride, oxalyl chloride, phosgene or chloroformic ester (Chem. Reviews 52, 237–416 (1953); Bhattacharya, Indian J. Chem. 6, 341–5, 1968) or when acylamino acids of the formula (XVI)

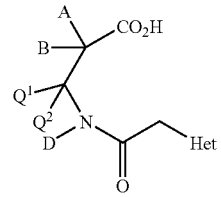
(XVI)

in which

A, B, D, $Q^1$, $Q^2$ and Het have the abovementioned meanings are esterified (Chem. Ind. (London) 1568 (1968)).

The compounds of the formula (XVI)

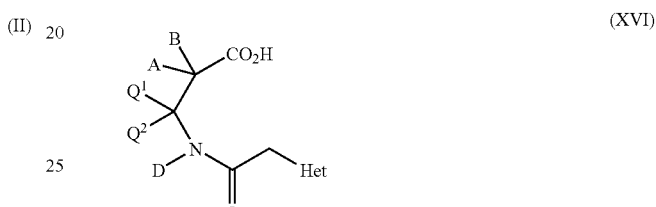
(XVI)

in which

A, B, D, $Q^1$, $Q^2$ and Het have the abovementioned meanings are new.

The compounds of the formula (XVI) are obtained when β-amino acids of the formula (XVII)

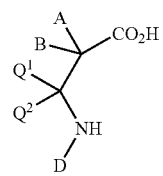
(XVII)

in which

A, B, $Q^1$, $Q^2$ and D have the abovementioned meanings are acylated with substituted hetaryl acetic acid derivatives of the formula (XV)

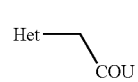
(XV)

in which

Het and U have the abovementioned meanings, for example following the method of Schotten-Baumann (Organikum [Organic Chemistry], VEB Deutscher Verlag der Wissenschaften, Berlin 1977, p. 505).

Some of the compounds of the formula (XV) are new. They can be synthesized by methods known in principle (see, for example, H. Henecka, Houben-Weyl, Methoden der Organischen Chemie [Methods in Organic Chemistry], Vol. 8, pp. 467–469 (1952)) or they are prepared in situ with the abovementioned reagents.

The compounds of the formula (XV) are obtained, for example, by reacting substituted hetaryl acetic acids of the formula (XVIII)

(XVIII)

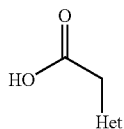

in which

Het has the abovementioned meaning with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons such as toluene or methylene chloride) at temperatures of from −20° C. to 150° C., preferably from −10° C. to 100° C.

Some of the hetaryl acetic acids of the formula (XVIII) are commercially available, some of them are known or can be prepared by processes known in principle (C. S. Rooney et al. J. Med. Chem. 26, 700–714 (1983); EP-A-368 592; M. S. Malamas et al. J. Med. Chem. 39, 237–246 (1996); J. L. Collins et al. J. Med. Chem. 41, 5037–5054 (1998); NL-A-66 14 130).

Some of the compounds of the formulae (XIV) and (XVII) are known and/or can be synthesized by known methods (see, for example, T. Suzuki et al., Synthetic Commun. 28, 701 (1998), R. Graf, Justus Liebigs Ann. Chem. 661, 111 (1963)).

Furthermore, the starting materials of the formula (II)

(II)

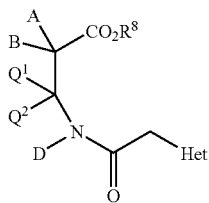

in which

A, B, D, $Q^1$, $Q^2$, Het and $R^8$ have the abovementioned meanings and which are used in the above process (A) can be prepared when aminonitriles of the formula (XIX)

(XIX)

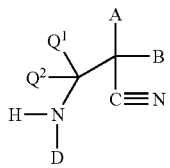

in which

A, B, $Q^1$, $Q^2$ and D have the abovementioned meanings are reacted with substituted hetaryl acetic acid derivatives of the formula (XV)

(XV)

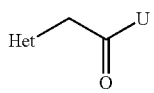

in which

Het and U have the abovementioned meanings to give compounds of the formula (XX)

(XX)

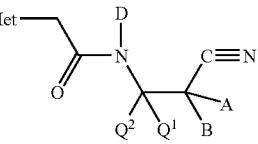

in which

A, B, D, $Q^1$, $Q^2$ and Het have the abovementioned meanings and subsequently subjecting the latter to acid alcoholysis.

The compounds of the formula (XX) are also new.

Some of the aminonitriles of the formula (XIX) are new and/or can be prepared by known processes (T. Suzuki et al., Chem. Pharm. Bull. 46, 1116 (1998)).

The compounds of the formula (III)

(III)

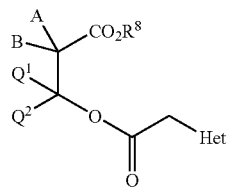

in which

A, B, $Q^1$, $Q^2$, Het and $R^8$ have the abovementioned meanings and which are required as starting materials in process (B) according to the invention are new.

The acylhydroxycarboxylic esters of the formula (III) are obtained, for example, when hydroxycarboxylic esters of the formula (XXI)

(XXI)

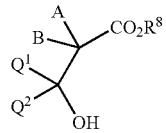

in which

A, B, $Q^1$, $Q^2$ and $R^8$ have the abovementioned meanings are acylated with substituted hetaryl acetic acid derivatives of the formula (XV)

(XV)

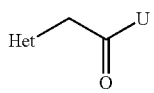

in which

Het and U have the abovementioned meaning (see preparation example of compounds of the formula (III)).

Some of the compounds of the formula (XXI) are known, commercially available or can be prepared by processes known in principle, for example by Refornatskij Synthesis (Organikum, VEB Deutscher Verlag der Wissenschaften, Berlin 1990, 18$^{th}$ Ed., p. 501 et seq.)

The acid halides of the formula (IV), carboxylic anhydrides of the formula (V), chloroformic esters or chloroformic thioesters of the formula (VI), chloromonothioformic esters or chlorodithioformic esters of the formula (VII), sulphonyl chlorides of the formula (VIII), phosphorus compounds of the formula (IX) and metal hydroxides, metal alkoxides or amines of the formulae (X) and (XI) and isocyanates of the formula (XII) and carbamoyl chlorides of the formula (XIII), all of which are furthermore required as starting materials for carrying out processes (C), (D), (E), (F), (G), (H) and (I) according to the invention, are generally known compounds of organic or inorganic chemistry.

Some of the compounds of the formulae (XIV), (XVII), (XVIII), (XIX) and (XXI) are commercially available, some of them are known and/or can be prepared by methods known in principle.

Process (A) is characterized in that compounds of the formula (II) in which A, B, D, $Q^1$, $Q^2$, Het and $R^8$ have the abovementioned meanings are subjected to an intramolecular condensation reaction in the presence of a base.

Diluents which can be employed in process (A) according to the invention are all inert organic solvents. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methyl-pyrrolidone, and also alcohols such as methanol, ethanol, propanol, isopropanol, butanol, isobutanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). Alkali metals such as sodium or potassium can furthermore be used. Amides and hydrides of alkali metals and alkaline earth metals, such as sodium amide, sodium hydride and calcium hydride are further possible materials which can be used, as are, moreover, alkali metal alkoxides such as sodium methoxide, sodium ethoxide and potassium tert-butoxide.

When carrying out process (A) according to the invention, the reaction temperatures can be varied within a substantial range. In general, the process is carried out at temperatures of between –80° C. and 180° C., preferably between –50° C. and 120° C.

Process (A) according to the invention is generally carried out under atmospheric pressure.

When carrying out process (A) according to the invention, the reactants of the formula (II) and the deprotonating bases are generally employed in approximately twice the equimolar amounts. However, it is possible to use one or the other reactants in a larger excess (up to 3 mol).

Process (B) is characterized in that compounds of the formula (III) in which A, B, $Q^1$, $Q^2$, Het and $R^8$ have the abovementioned meanings are subjected to an intramolecular condensation reaction in the presence of a diluent and in the presence of a base.

Diluents which can be employed in process (B) according to the invention are all inert organic solvents. The following can preferably be used: hydrocarbons such as toluene and xylene, furthermore ethers such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols such as methanol, ethanol, propanol, isopropanol, butanol, isobutanol and tert-butanol.

Bases (deprotonating agents) which can be employed when carrying out process (B) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase-transfer catalysts such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)-amine). Alkali metals such as sodium or potassium can furthermore be used. Amides and hydrides of alkali metals and alkaline earth metals, such as sodium amide, sodium hydride and calcium hydride are further possible materials which can be used, as are, moreover, alkali metal alkoxides such as sodium methoxide, sodium ethoxide and potassium tert-butoxide.

When carrying out process (B) according to the invention, the reaction temperatures can be varied within a substantial range. In general, the process is carried out at temperatures of between –80° C. and 180° C., preferably between –50° C. and 120° C.

Process (B) according to the invention is generally carried out under atmospheric pressure.

When carrying out process (B) according to the invention, the reactants of the formula (II) and the deprotonating bases are generally employed in approximately twice the equimolar amounts. However, it is possible to use one or the other reactants in a larger excess (up to 3 mol).

Process (C-α) is characterized in that compounds of the formulae (I-1-a) to (I-2-a) are in each case reacted with carboxylic acid halides of the formula (IV), if appropriate in the presence of a diluent and if appropriate in the presence of an acid binder.

Diluents which can be employed in process (C-α) according to the invention are all solvents which are inert to the acid halides. The following can preferably be used: hydrocarbons such as benzine, benzene, toluene, xylene and tetralin, furthermore halogenohydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic esters such as ethyl acetate, nitriles such as acetonitrile, or else strongly polar solvents such as dimethylformamide, dimethylacetamide, dimethyl sulphoxide and sulpholane. If the acid halide is sufficiently stable to hydrolysis, the reaction may also be carried out in the presence of water.

Suitable acid binders when carrying out the reaction in accordance with process (C-α) according to the invention are all customary acid acceptors. The following can preferably be used: tertiary amines such as triethylamine, pyridine, diazabicyclooctane (DABCO), diazabicycloundecene (DBU), diazabicyclononene (DBN), Hünig Base and N,N-dimethyl-anilin, furthermore alkali metal oxides such as magnesium oxide and calcium oxide, moreover alkali metal carbonates and alkaline earth metal carbonates such as sodium carbonate, potassium carbonate and calcium carbonate, and alkali metal hydroxides such as sodium hydroxide and potassium hydroxide.

When carrying out process (C-α) according to the invention, the reaction temperatures may be varied within a substantial range. In general, the process is carried out at temperatures of between –20° C. and +150° C., preferably between 0° C. and 100° C.

When carrying out process (C-α) according to the invention, the starting materials of the formulae (I-1-a) to (I-2-a) and the carboxylic acid halide of the formula (IV) are generally in each case used in approximately equivalent amounts. However, it is also possible to employ the carboxylic acid halides in a larger excess (of up to 5 mol). Work-up is carried out by customary methods.

Process (C-β) is characterized in that compounds of the formulae (I-1-a) to (I-2-a) are reacted with carboxylic anhydrides of the formula (V), if appropriate in the presence of a diluent and if appropriate in the presence of an acid binder.

Diluents which can be used in process (C-β) according to the invention are preferably those diluents which are also preferably suitable when acid halides are used. Besides, a carboxylic anhydride used in excess may also simultaneously act as the diluent.

Suitable acid binders which are optionally added in process (C-β) are preferably those acid binders which are also preferably suitable when acid halides are used.

When carrying out process (C-β), the reaction temperatures can be varied within a substantial range. In general, the process is carried out at temperatures of between −20° C. and +150° C., preferably between 0° C. and 100° C.

When carrying out process (C-β) according to the invention, the starting materials of the formulae (I-1-a) to (I-2-a) and the carboxylic anhydride of the formula (V) are generally employed in each case in approximately equivalent amounts. However, it is also possible to employ the carboxylic anhydride in a larger excess (of up to 5 mol). Work-up is carried out by customary methods.

In general, a procedure is followed in which diluent, excess carboxylic anhydride and the carboxylic acid which forms are removed by distillation or by washing with an organic solvent or with water.

Process (D) is characterized in that compounds of the formulae (I-1-a) to (I-2-a) are reacted in each case with chloroformic esters or chloroformic thioesters of the formula (VII), if appropriate in the presence of a diluent and if appropriate in the presence of acid binder.

Suitable acid binders for the reaction in accordance with process (D) according to the invention are all customary acid acceptors. The following can preferably be used: tertiary amines such as triethylamine, pyridine, DABCO, DBU, DBA, Hünig base and N,N-dimethyl-anilin, furthermore alkali metal oxides such as magnesium oxide and calcium oxide, moreover alkali metal carbonates and alkaline earth metal carbonates such as sodium carbonate, potassium carbonate and calcium carbonate, and also alkali metal hydroxides such as sodium hydroxide and potassium hydroxide.

Diluents which can be employed in process (D) according to the invention are all solvents which are inert to the chloroformic esters or chloroformic thioesters. The following can preferably be used: hydrocarbons such as benzine, benzene, toluene, xylene and tetraline, furthermore halogeno-hydrocarbons such as methylene chloride, chloroform, carbon tetrachloride, chlorobenzene and o-dichlorobenzene, moreover ketones such as acetone and methyl isopropyl ketone, furthermore ethers such as diethyl ether, tetrahydrofuran and dioxane, in addition carboxylic esters such as ethyl acetate, nitriles such as acetonitrile and also strongly polar solvents such as dimethylformamide, dimethylacetamide, dimethyl sulphoxide and sulpholane.

When carrying out process (D) according to the invention, the reaction temperatures can be varied within a substantial range. If the process is carried out in the presence of a diluent and of an acid binder, the reaction temperatures are generally between −20° C. and +100° C., preferably between 0° C. and 50° C.

Process (D) according to the invention is generally carried out under atmospheric pressure.

When carrying out process (D) according to the invention, the starting materials of the formulae (I-1-a) to (I-2-a) and the corresponding chloroformic ester or chloroformic thioester of the formula (VI) are generally used in each case in approximately equivalent amounts. However, it is also possible to employ one or the other reactant in a larger excess (of up to 2 mol). Work-up is carried out by customary methods. In general, a procedure is followed in which the salts which have precipitated are removed and the reaction mixture which remains is concentrated by stripping off the diluent.

Process (E) according to the invention is characterized in that compounds of the formulae (I-1-a) to (I-2-a) are reacted in each case with compounds of the formula (VII) in the presence of a diluent and, if appropriate, in the presence of an acid binder.

In preparation process (E), approximately 1 mol of chloromonothioformic ester or chlorodithioformic ester of the formula (VII) is reacted at from 0 to 120° C., preferably at from 20 to 60° C., per mole of starting compound of the formulae (I-1-a) to (I-2-a).

Suitable diluents which are optionally added are all inert polar organic solvents such as nitrites, esters, ethers, amides, sulphones, sulphoxides, but also halogenoalkanes.

Substances which are preferably employed are acetonitrile, ethyl acetate, dimethyl sulphoxide, tetrahydrofuran, dimethylformamide or methylene chloride.

If, in a preferred embodiment, the enolate salt of the compounds (I-1-a) to (I-2-a) by addition of strong deprotonating agents such as, for example, sodium hydride or potassium tertiary-butylate, the further addition of acid binders can be dispensed with.

If acid binders are employed, then customary inorganic or organic bases are suitable, with sodium hydroxide, sodium carbonate, potassium carbonate, pyridine and triethylamine being mentioned by way of example.

The reaction can be carried out under atmospheric pressure or under elevated pressure, preferably under atmospheric pressure. Work-up is carried out by customary methods.

Process (F) according to the invention is characterized in that compounds of the formulae (I-1-a) to (I-2-a) are reacted in each case with sulphonyl chloride of the formula (VIII), if appropriate in the presence of a diluent and if appropriate in the presence of an acid binder.

In preparation process (F), approximately 1 mol of sulphonyl chloride of the formula (VIII) is reacted at from −20 to 150° C., preferably at from 20 to 70° C., per mole of starting compound of the formulae (I-1-a) to (I-2-a).

Suitable diluents which are optionally added are all inert polar organic solvents such as nitriles, esters, ethers, amides, nitriles, sulphones, sulphoxides or halogenated hydrocarbons such as methylene chloride.

Substances which are preferably employed are acetonitrile, ethyl acetate, dimethyl sulphoxide, tetrahydrofuran, dimethylformamide, methylene chloride.

If, in a preferred embodiment, the enolate salt of the compounds. (I-1-a) to (I-2-a) is synthesized by addition of strong deprotonating agents (such as, for example, sodium hydride or potassium tertiary-butoxide), the further addition of acid binders can be dispensed with.

If acid binders are employed, customary inorganic or organic bases are suitable, with sodium hydroxide, sodium carbonate, potassium carbonate, pyridine and triethylamine being mentioned by way of example.

The reaction can be carried out under atmospheric pressure or under elevated pressure, preferably under atmospheric pressure. Work-up is carried out by customary methods.

Process (G) according to the invention is characterized in that compounds of the formulae (I-1-a) to (I-2-a) are reacted in each case with phosphorus compounds of the formula (IX), if appropriate in the presence of a diluent and if appropriate in the presence of an acid binder.

In preparation process (G), 1 to 2, preferably 1 to 1.3, mole of the phosphorus compound of the formula (IX) are reacted at temperatures of between −40° C. and 150° C., preferably between −10 and 110° C., per mole of the compounds (I-1-a) to (I-2-a) in order to obtain compounds of the formulae (I-1-e) to (I-2-e).

Suitable diluents which are optionally added are all inert polar organic solvents such as ethers, amides, nitrites, alcohols, sulphides, sulphones, sulphoxides and the like.

Substances which are preferably employed are acetonitrile, dimethyl sulphoxide, tetrahydrofuran, dimethylformamide, methylene chloride.

Suitable acid binders which are optionally added are customary inorganic or organic bases such as hydroxides, carbonates or amines. Examples which may be mentioned are sodium hydroxide, sodium carbonate, potassium carbonate, pyridine, triethylamine.

The reaction can be carried out under atmospheric pressure or under elevated pressure, preferably under atmospheric pressure. Work-up is carried out by customary methods of organic chemistry. The resulting end products are preferably purified by crystallization, chromatography or by what is known as "incipient distillation", that is to say removal of the volatile components in vacuo.

Process (H) is characterized in that compounds of the formulae (I-1-a) to (I-2-a) are reacted with metal hydroxides or metal alkoxides of the formula (X) or amines of the formula (XI), if appropriate in the presence of a diluent.

Diluents which can be employed in process (I) according to the invention are, preferably, ethers such, as tetrahydrofuran, dioxane, diethyl ether, or else alcohols such as methanol, ethanol, isopropanol, but also water.

Process (H) according to the invention is generally carried out under atmospheric pressure.

In general, the reaction temperatures are between −20° C. and 100° C., preferably between 0° C. and 50° C.

Process (I) according to the invention is characterized in that compounds of the formulae (I-1-a) to (I-2-a) are reacted in each case with compounds of the formula (XII) (I-α), if, appropriate in the presence of a diluent and if appropriate in the presence of a catalyst, or (I-β) with compounds of the formula (XIII), if appropriate in the presence of a diluent and if appropriate in the presence of an acid binder.

When carrying out preparation process (I-α), approximately 1 mol of isocyanate of the formula (XII) is reacted at from 0 to 100° C., preferably at from 20 to 50° C., per mole of starting compound of the formulae (I-1-a) to (I-2-a).

Suitable diluents which are optionally added are all inert organic solvents, such as ethers, amides, nitrites, sulphones, sulphoxides.

If appropriate, catalysts may be added to accelerate the reaction. Catalysts which can be employed very advantageously are organotin compounds such as, for example, dibutyltin dilaurate. The process is preferably carried out under atmospheric pressure.

When carrying out preparation process (I-β), approximately 1 mol of carbamoyl chloride of the formula (XIII) is reacted at from −20 to 150° C., preferably at from 0 to 70° C., per mole of starting compound of the formulae (I-1-a) to (I-2-a).

Suitable diluents which are optionally added are all inert polar organic solvents such as nitriles, esters, ethers, amides, sulphones, sulphoxides or halogenated hydrocarbons.

The substances which are preferably employed are acetonitrile, ethyl acetate, dimethyl sulphoxide, tetrahydrofuran, dimethylformamide or methylene chloride.

If, in a preferred embodiment, the enolate salt of the compound (I-1-a) to (I-2-a) is synthesized by adding strong deprotonating agents (such as, for example, sodium hydride or potassium tertiary-butoxide), the further addition of acid binders can be dispensed with.

The active compounds are suitable for controlling animal pests, in particular insects, arachnids and nematodes found in agriculture, in forests, in the protection of stored products and materials, and in the hygiene sector, while being well tolerated by plants and exhibiting a favourable toxicity to warm-blooded species. They can preferably be employed as crop protection agents. They are active against normally sensitive and resistant species and against all individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella accidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica*

*alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderna* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon soistitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

If appropriate, the compounds according to the invention, in specific concentrations or at specific application rates, can also be used as herbicides and microbicides, for example as fungicides, antimycotics and bactericides. If appropriate, they may also be used as intermediates or precursors for the synthesis of further active compounds.

All plants and plant parts can be treated in accordance with the invention. Plants are understood, in the present context, as meaning all plants and plant populations such as desired and undesired wild plants or crop plants (including naturally occurring crop plants). Crop plants may be plants which can be obtained by conventional breeding and optimization methods or else by biotechnological and recombinant methods or combinations of these methods, including the transgenic plants and the plant varieties which can be protected or which cannot be protected by Plant Breeders' Rights. Plant parts are understood as meaning all aerial and subterraneous parts and organs of the plants, such as shoot, leaf, flower and root, with leaves, needles, stems, stalks, flowers, fruiting bodies, fruits and seeds and also roots, tubers and rhizomes being mentioned by way of example. The plant parts also include harvested material and vegetative and generative propagation material, for example cuttings, tubers, rhizomes, shoots and seeds.

The treatment according to the invention of the plants and plant parts with the active compounds is affected directly or by acting on their environment or the surroundings in which they grow or in which they are stored, using customary treatment methods, for example by immersion, spraying, atomizing, forging, spreading, brushing on and, in the case of propagation material, in particular seeds, furthermore by coating with one or more coats.

The active compounds can be converted into the customary formulations such as solutions, emulsions, wettable powders, suspensions, powders, dusts, pastes, soluble powders, granules, suspended emulsion concentrates, natural and synthetic materials impregnated with active compounds, and microencapsulations and polymeric substances.

These formulations are prepared in the known manner, for example by mixing the active compounds with extenders, that is to say liquid solvents and/or solid carriers, if appropriate using surfactants, that is to say emulsifiers and/or dispersants and/or foam formers.

If water is used as extender, it is also possible, for example, to use organic solvents as auxiliary solvents. Suitable liquid solvents are essentially: aromatics such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane, or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are:

for example, ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example, crushed and fractionated natural rocks such as calcite, marble, pumice, sepiolite, dolomite, and synthetic granules of inorganic or organic meals and granules of organic material such as sawdust, coconut shells, maize cobs and tobacco stalks; suitable emulsifiers and/or foam formers are: for example, non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example, lignin-sulphite waste liquors and methylcellulose.

Adhesives such as carboxymethylcellulose, natural and synthetic polymers in the form of powders, granules or latices such as gum arabic, polyvinyl alcohol, polyvinyl acetate, and natural phospholipids such as cephalins and lecithins and synthetic phospholipids may be used in the formulations. Other additives may be mineral and vegetable oils.

Colorants such as inorganic pigments, for example iron oxide, titanium oxide, Prussian Blue, and organic dyestuffs such as alizarin, azo and metal phthalocyanin dyes and micronutrients such as salts of iron, manganese, boron, copper, cobalt, molybdenum and zinc may be used.

In general, the formulations comprise between 0.1 and 95% by weight of active compound, preferably between 0.5 and 90%.

The active compounds according to the invention, as such or in their formulations, may also be used in a mixture with known fungicides, bactericides, acaridices, nematicides or insecticides, for example to widen the spectrum of action or to prevent the build-up of resistance. In many cases, synergistic effects result, i.e. the activity of the mixture exceeds the activity of the individual components.

Examples of suitable components in mixtures are the following compounds:

Fungicides aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvone, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamin, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxyde, ferbam, ferimzone, fluazinam, flumetover, fluoromid, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazol, imazalil, imibenconazole, iminoctadine, iminoctadine albesilate, iminoctadine triacetate, iodocarb, ipconazole, iprobenfos (IBP), iprodione, irumamycin, isoprothiolan, isovaledione, kasugamycin, kresoxim-methyl, copper preparations such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulphocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiine, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamid, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]-carbonyl]-propyl}-carbonate 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-a-D-glucopyranosyl]-amino]4-methoxy-1H-pyrrolo[2,3-d]pyrimidine-5-carbonitrile, 2-aminobutane, 2-bromo-2-(brommethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol(OPP), 3,4-dichloro-1-[4-(difluoromethoxy)-phenyl]-1H-pyrrole-2,5-dione, 3,5-dichloro-N-[cyano[(1-methyl-2-propynyl)-oxy]-methyl]-benzamide, 3-(1,1-dimethylpropyl-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4,5]decane-2-methanamine, 8-hydroxyquinolin sulphate, 9H-xanthene-9-carboxylic acid 2-[(phenylamino)-carbonyl]-hydrazide, bis-(1-methylethyl)-3-methyl-4-[(3-methylbenzoyl)-oxy]-2,5-thiophene dicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine hydrochloride, Ethyl [(4-chlorophenyl)-azo]-cyanoacetate, potassium hydrogen carbonate, sodium methane tetrathiolate, methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyrdinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'methoxymethanimidamide,
sodium N-formyl-N-hydroxy-DL-alaninate,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
4-[3,4-dimethoxyphenyl)-3-(4-fluorophenyl)-acryloyl]-morpholine Bactericides bronopol, dichlorophen, nitrapyrin, nickel dimethyldithiocarbamate, kasugamycin, oc-thilinone, furancarboxylic acid, oxytetracyclin, probenazole, streptomycin, tecloftalam, copper sulphate and other copper preparations.

Insecticides/Acaricides/Nematicides abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben,
cadusafos, carbaryl, carbofuran, carbophenothion, carbosulphan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cisresmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, dicofol, diflubenzuron, dimethoate, dimethylvinphos, diofenolan, disulfoton, docusate-sodium, dofenapyn,
eflusilanate, emamectin, empenthrin, endosulfan, *Entomophthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb,
granulosis viruses
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses
lambda-cyhalothrin, lufenuron
malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos,
naled, nitenpyram, nithiazine, novaluron
ometothoate, oxamyl, oxydemethon M
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen,
quinalphos,
ribavirin
salithion, sebufos, silafluofen, spinosad, spirodiclofen, sulfotep, suiprofos,
tau-fluvalinate, tebufenozide, tebufenpyrad, tebupirimphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii* YI 5302
zeta-cyperrnethrin, zolaprofos (1R-cis)-[5-(phenylmethyl)-3-furanyl]-methyl-3-[(dihydro-2-oxo-3(2H)-furanylidene)-methyl]2,2-dimethylcyclopropanecarboxylate (3-phenoxyphenyl)-methyl 2,2,3,3-tetramethylcyclopropanecarboxylate 1-[(2-chloro-5-thiazolyl)methyl]tetrahydro-3,5-dimethyl-N-nitro-1,3,5-triazin-2(1H)-imine
2-(2-chloro-6-fluorophenyl)-4-[4-(1,1-dimethylethyl)phenyl]-4,5-dihydro-oxazole
2-(acetyloxy)-3-dodecyl-1,4-naphthalenedione
2-chloro-N-[[[4-(1-phenylethoxy)-phenyl]-amino]-carbonyl]-benzamide
2-chloro-N-[[[4-(2,2-dichloro-1,1-difluorethoxy)-phenyl]-amino]-carbonyl]-benzamide
3-methylphenyl propylcarbamate
4-[4-(4-ethoxyphenyl)-4-methylpentyl]-1-fluoro-2-phenoxy-benzene
4-chloro-2-(1,1-dimethylethyl)-5-[[2-(2,6-dimethyl-4-phenoxyphenoxy)ethyl]thio]-3(2H)-pyridazinone
4-chloro-2-(2-chloro-2-methylpropyl)-5-[(6-iodo-3-pyridinyl)methoxy]-3(2H)-pyridazinone
4-chloro-5-[(6-chloro-3-pyridinyl)methoxy]-2-(3,4-dichlorphenyl)-3(2H)-pyridazinone
*Bacillus thuringiensis* strain EG-2348
[2-benzoyl-1-(1,1-dimethylethyl)]-benzohydrazide 2,2-dimethyl-3-(2,4-dichlorophenyl)-2-oxo-1-oxaspiro[4.5]
dec-3-en-4-yl-ester butanoate
[3-[(6-chloro-3-pyridinyl)methyl]-2-thiazolidinylidene]-cyanamide
dihydro-2-(nitromethylene)-2H-1,3-thiazine-3(4H)-carboxaldehyde
ethyl [2-[[1,6-dihydro-6-oxo-1-(phenylmethyl)-4-pyridazinyl]oxy]ethyl]-carbamate
N-(3,4,4-trifluoro-1-oxo-3-butenyl)-glycine
N-(4-chlorophenyl)-3-[4-(difluoromethoxy)phenyl]-4,5-dihydro-4-phenyl-1H-pyrazole-1-carboxamide
N-[(2-chloro-5-thiazolyl)methyl]-N'-methyl-N"-nitroguanidine
N-methyl-N'-(1-methyl-2-propenyl)-1,2-hydrazine dicarbothioamide
N-methyl-N'-2-propenyl-1,2-hydrazine dicarbothioamide
O,O-diethyl [2-(dipropylamino)-2-oxoethyl]-ethylphosphoramidothioate
N-cyanomethyl-4-trifluoromethyl-nicotinamide
3,5-dichloro-1-(3,3-dichloro-2-propenyloxy)-4-[3-(5-trifluoromethylpyridin-2-yloxy)-propoxy]-benzene A mixture with other known active compounds such as herbicides or with fertilizers and growth regulators is also possible.

When employed as insecticides, the active compounds according to the invention, in their commercially available formulations and in the use forms prepared from these formulations, may furthermore be present in a mixture with synergists. Synergists are compounds by which the action of the active compounds is increased without it being necessary for the synergist added to be active itself.

The active compound content of the use forms prepared from the commerically available formulations can vary within wide ranges. The active compound concentration of the use forms can be from 0.0000001 to 95% by weight of active compound, preferably between 0.0001 and 1% by weight.

They are applied in a customary manner adapted to suit the use forms.

When used against hygiene and stored-product pests, the active compound is distinguished by outstanding residual action on wood and clay and by good stability to alkali on limed substrates.

As already mentioned above, all plants and their parts may be treated in accordance with the invention. In a preferred embodiment, plant species and plant varieties which occur in the wild or which have been obtained by conventional biological breeding methods, such as hybridization or protoplast fusion, and parts of these plant species and plant varieties are treated. In another preferred embodiment, transgenic plants and plant varieties which have been obtained by genetic engineering methods, if appropriate in combination with conventional methods (genetic modified organisms), and parts of these plants and plant varieties are treated. The term "parts" and "parts of plants" or "plant parts" has been illustrated above.

Plants which are especially preferably treated in accordance with the invention are those of the plant varieties which are commercially available or in use. Plant varieties are understood as meaning plants with novel properties ("traits") which have been bred by conventional breeding, by mutagenesis and also be recombinant DNA techniques. They can take the form of varieties, biotypes and genotypes.

Depending on the plant species or plant varieties, their location and growth conditions (soils, climate, vegetation period, nutrition), superadditive ("synergistic") effects may also occur as a result of the treatment in accordance with the invention. Thus, for example, reduced application rates and/or a widened spectrum of action and/or an increased action of the substances and compositions which can be used in accordance with the invention, better plant growth, increased tolerance to high or low temperatures, increased tolerance to drought or to water or soil salinity, increased flowering performance, facilitated harvesting, accelerated maturation, higher yields, higher quality and/or higher nutritional value of the harvested products, better storability and/or processability of the harvested products are possible, which exceed the actual effects to be expected.

The preferred transgenic plants or plant varieties (obtained by recombinant methods) to be treated in accordance with the invention include all plants which, owing to modification by recombinant means, contain genetic material which imparts particular advantageous valuable traits to these plants. Examples of such properties are better plant growth, increased tolerance to high or low temperatures, increased tolerance to drought or to water or soil salinity, increased flowering performance, facilitated harvesting, accelerated maturation, higher yields, higher quality and/or higher nutritional value of the harvested products, better storability and/or processability of the harvested products. Other especially emphasized examples of such traits are an increased defence of the plants against animal and microbial pests such as against insects, mites, phytopathogenic fungi, bacteria and/or viruses, and an increased tolerance of the plants to certain herbicidal active compounds. Examples of transgenic plants which may be mentioned are important crop plants such as cereals (wheat, rice), maize, soya, potato, cotton, oil seed rape and fruit plants (with the fruits apples, pears, citrus fruit and grapes), with particular emphasis being placed on maize, soya, potato, cotton and oil seed rape. Traits which are particularly emphasized are the increased defence of the plants against insects by toxins formed in the plants, in particular those which are generated by the genetic material from *Bacillus thuringiensis* (for example, by the genes CryIA(a), CryIA(b), CryIA(c), CryIIA, CryIIIA, CryIIIB2, Cry9c Cry2Ab, Cry3Bb and CryIF and their combinations) in the plants (hereinbelow "Bt plants"). Other traits which are particularly emphasized are the increased defence of plants against fungi, bacteria and viruses by systemic acquired resistance (SAR), systemin, phytoalexins, elicitors and resistance genes and correspondingly expressed proteins and toxins. Other traits which are furthermore particularly emphasized are the increased tolerance of the plants to certain herbicidal active compounds, for example imidazolinones, sulphonyl ureas, glyphosate or phosphinothricin (for example "PAT" gene). The genes which impart each of the desired traits may also occur in combination with each other in the transgenic plants. Examples of "Bt plants" which may be mentioned are varieties of maize, cotton, soya and potato which are commercially available under the trade names YIELD GARD® (for example, maize, cotton, soya), KnockOut® (for example maize), StarLink® (for example maize), Bollgard® (cotton), Nucotn® (cotton) and NewLeaf® (potato). Examples of herbicide-tolerant plants which may be mentioned are varieties of maize, cotton and soya which are commercially available under the trade names Roundup Ready® (tolerance to glyphosate, for example maize, cotton, soya), Liberty Link® (tolerance to phosphinothricin, for example oil seed rape), IMI® (tolerance to imidazolinones) and STS® (tolerance to sulphonyl ureas, for example maize). Herbicide-resistant plants (bred conventionally for herbicide tolerance) which may also be mentioned are the varieties which are commercially available under the name Clearfield® (for example maize). Naturally, these statements also apply to plant varieties which will be developed in the future or which will be marketed in the future and which have these genetic traits, or genetic traits to be developed in the future.

The plants stated can be treated particularly advantageously in accordance with the invention with the compounds of the general formula I or the active compound mixtures according to the invention. The preferred ranges stated above for the active compounds or mixtures also apply to the treatment of these plants. The treatment of plants with the compounds or mixtures specifically stated in the present text may be particularly emphasized.

The active compounds according to the invention not only act against plant, hygiene and stored-product pests, but also, in the veterinary medicine sector, against animal parasites (ectoparasites) such as hard ticks, soft ticks, scab mites, harvest mites, flies (stinging and licking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattella germanica, Supella* spp.

From the subclass of the Acaria (Acarida) and the orders of the Metastigmata and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropodes which attack agricultural livestock such as, for example, cattle, sheep, goats, horses, pigs, donkeys, camels, buffalo, rabbits, chickens, turkeys, ducks, geese, honeybees, other domestic animals such as, for example, dogs, cats, cage birds, aquarium fish and what are known as experimental animals such as, for example, hamsters, guineapigs, rats and mice. By controlling these arthropodes, it is intended to reduce deaths and reduced performance (in meat, milk, wool, hides, eggs, honey and the like) so that more economic and simpler animal keeping is possible by employing the active compounds according to the invention.

The active compounds according to the invention are applied in the veterinary sector in a known manner by enteral administration in the form of, for example, tablets, capsules, drinks, drenches, granules, pastes, bolisis, the feed-through method, suppositories, by parenteral administration such as, for example, by injections (intramuscular, subcutaneous, intravenous, intraperitoneal and the like), implants, by nasal application, by dermal application in the form of, for example, immersing or bathing (dipping), spraying, pouring-on and spotting-on, washing, dusting and with the aid of shaped articles comprising active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

Moreover, it has been found that the compound according to the invention has a potent insecticidal action against insects which destroy industrial materials.

The following insects may be mentioned by way of example and by preference, but without limitation:

Beetles such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenoptera such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptoternes formosanus.*

Bristle tails such as *Lepisma saccharina*.

Industrial materials in the present context are understood as meaning non-live materials such as, preferably, polymers, adhesives, glues, paper and board, leather, wood, tin products and paints.

The material to be protected from insect attack is very especially preferably wood and timber products.

Wood and timber products which can be protected by the agent according to the invention or mixtures comprising it are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compounds can be used as such, in the form of concentrates or generally customary formulations such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if desired desiccants and UV stabilizers, and if desired colorants and pigments and other processing aids.

The insecticidal compositions or concentrates used for the protection of wood and timber products comprise the active compound according to the invention in a concentration of from 0.0001 to 95% by weight, in particular from 0.001 to 60% by weight.

The amount of the compositions or concentrates employed depends on the species and the abundance of the insects and of the medium. The optimal quantity to be employed can be determined in each case upon application by test series. In general, however, it will suffice to employ from 0.0001 to 20% by weight, preferably from 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oil or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkyl benzene.

Mineral oils which are advantageously used are those with a boiling range of from 170 to 220° C., white spirit with a boiling range of from 170 to 220° C., spindle oil with a boiling range of from 250 to 350° C., petroleum and aromatics with a boiling range of from 160 to 280° C., oil of turpentine, and the like.

In a preferred embodiment, liquid aliphatic hydrocarbons with a boiling range of from 180 to 210° C. or high-boiling mixtures of aromatic and aliphatic hydrocarbons with a boiling range of from 180 to 220° C. and/or spindle oil and/or monochloronaphthalene, preferably α-monochloronaphthalene, are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the insecticide/fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellents, odour-masking agents, and inhibitors or anticorrosive agents and the like, all of which are known per se, can be employed.

In accordance with the invention, the composition or the concentrate preferably comprises, as organochemical binder, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or a plasticizer (mixture). These additives are intended to prevent volatilization of the active compounds, and also crystallization or precipitation. They preferably replace from 0.01 to 30% of the binder (based on 100% of the binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylene benzophenone.

Other suitable solvents or diluents are, in particular, also water, if appropriate in a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

If appropriate, the compositions which are ready for use can additionally comprise further insecticides and, if appropriate, additionally one or more fungicides.

Additional components in mixtures which are suitable are, preferably, the insecticides and fungicides stated in WO 94/29 268. The compounds stated in this document are expressly part of the present application.

Very especially preferred components in mixtures which can be used are insecticides such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and fungicides such as epoxyconazole, hexaconazole, azaconazole, propiconazole, tebuconazole, cyproconazole, metconazole, imazalil, dichlorfluanid, tolylfluanid, 3-iod-2-propinyl butylcarbamate, N-octyl-isothiazolin-3-one and 4,5-dichloro-N-octylisothiazolin-3-one.

The compounds according to the invention can simultaneously also be employed for protecting objects which come into contact with salt water and brackish water, such as hulls, screens, nets, buildings, moorings and signalling systems, from fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term *Cirripedia* (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, the use of heavy metals such as, for example, in bis(trialkyltin) sulphides, tri-n-butyltin laurate, tri-n-butyltin chloride, copper (I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of pyridine-2-thiol 1-oxide, bisdimethyldithiocarbamoylzinc ethylenebisthiocarbamate, zinc oxide, copper(I) ethylenebisthiocarbamate, copper thiocyanate, copper naphthenate and tributyltin halides can be dispensed with, or the concentration of these compounds can be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:

Algicides such as 2-tert-butylamino-4-cyclopropylamino-6-methylthio-1,3, 5-triazine, dichlorophen, diuron, endothal, fentin acetate, isoproturon, methabenzthiazuron, oxyfluorfen, quinoclamine and terbutryn;

Fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propi-conazole and tebuconazole;

Molluscicides such as fentin acetate, metaldehyde, methiocarb, niclosamid, thiodicarb and trimethacrb; or traditional antifouling active compounds such as 4,5-dichloro-2-octyl-4-isothiazolin-3-one, diiodomethylparatryl sulphone, 2 -(N,N-di-methylthiocarbamoylthio)-5-nitrothiazyl, potassium salts, copper salts, sodium salts and zinc salts of pyridine-2-thiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleinimide.

The antifouling compositions used comprise the active compound according to the invention of the compounds according to the invention in a concentration of from 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and the insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably soluble in salt water. Paints may furthermore comprise materials such as kolophonium to allow controlled release of the active compounds.

Furthermore, the paints may comprise plasticizers, modifiers which affect the Theological properties and other conventional constituents. The compounds according to the invention or the abovementioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests, either alone or in combination with other active compounds and auxiliaries. They are effective against sensitive and resistant species and against all developmental stages. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, Avicularidae, Araneidae.

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

Application in the field of domestic insecticides is affected alone or in combination with other suitable active compounds such as phosphoric esters, carbamates, pyrethroides, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free or passive evaporation systems, moth papers, moth bags and moth gels, as granules or dusts, in baits for spreading or in bait stations.

The active compounds according to the invention can also be used as defoliants, desiccants, haulm killers and, especially, as weedkillers. By weeds, in the broadest sense, are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, in lawns, turf and pastures, and for selective weed control in annual crops.

The compounds of the formula (I) according to the invention show a potent herbicidal activity and a broad spectrum of action when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds according to the invention can also be used for controlling animal pests and fungal or bacterial plant diseases. If appropriate, they can also be used as intermediates or precursors for the synthesis of further active compounds.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as cosolvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example, ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example, crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example, non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example, lignin-sulphite waste liquors and methylcellulose.

Adhesives such as carboxymethylcellulose and natural and synthetic polymers in the form of powders, granules or latices such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides and/or with substances which improve the crop plant tolerance ("safeners"), ready mixes or tank mixes being possible. Thus, mixtures with weed killers comprising one or more known herbicides and a safener are also possible.

Suitable herbicides for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, di-allate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendi-methalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyiibuticarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, tri-allate, triasulfuron, tribenuron (-methyl), triclopyr, tridiphane, trifluralin, trifloxysulfuron, triflusulfuron (-methyl), tritosulfuron.

Furthermore, safeners which are suitable for the mixtures are known safeners, for example:

AD-67, BAS-145138, benoxacor, cloquintocet (-mexyl), cyometrinil, 2,4-D, DKA-24, dichlormid, dymron, fenclorim, fenchlorazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

Mixtures with other known active compounds such as fungicides, insecticides, acaricides, nematicides, bird repellants, plant nutrients and soil conditioners are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 1 g and 10 kg of active compound per hectare of soil surface, preferably between 5 g and 5 kg per ha.

The substances according to the invention exhibit a potent microbicidal action and can be employed for controlling undesired microorganisms, such as fungi and bacteria, in crop protection and in the protection of materials.

Fungicidal agents are employed in crop protection for controlling *Plasmodiophoromycetes, Oomycetes, Chytridiomycetes, Zygomycetes, Ascomycetes, Basidiomycetes* and *Deuteromycetes*.

Bactericidal agents are employed in crop protection for controlling *Pseudomonadaceae, Rhizobiaceae, Enterobacteriaceae, Corynebacteriaceae* and *Streptomycetaceae*.

Some pathogens causing fungal and bacterial diseases which come under the generic names listed above may be mentioned as examples, but not by way of limitation:

*Xanthomonas* species, such as, for example, *Xanthomonas campestris* pv. *oryzae;*

*Pseudomonas* species, such as, for example, *Pseudomonas syringae* pv. *lachrymans;*

*Erwinia* species, such as, for example, *Erwinia amylovora;*

*Pythium* species, such as, for example, *Pythium ultimum;*

*Phytophthora* species, such as, for example, *Phytophthora infestans;*

*Pseudoperonospora* species, such as, for example, *Pseudoperonospora humuli* or *Pseudoperonospora cubensis;*

*Plasmopara* species, such as, for example, *Plasmopara viticola;*

*Bremia* species, such as, for example, *Bremia lactucae;*

*Peronospora* species, such as, for example, *Peronospora pisi* or *P. brassicae;*

*Erysiphe* species, such as, for example, *Erysiphe graminis;*

*Sphaerotheca* species, such as, for example, *Sphaerotheca fuliginea;*

*Podosphaera* species, such as, for example, *Podosphaera leucotricha;*

*Venturia* species, such as, for example, *Venturia inaequalis;*

*Pyrenophora* species, such as, for example, *Pyrenophora teres* or *P. graminea* (conidial form: *Drechslera,* syn: *Helminthosporium*);

*Cochliobolus* species, such as, for example, *Cochliobolus sativus* (conidial form: *Drechslera,* syn: *Helminthosporium*);

*Uromyces* species, such as, for example, *Uromyces appendiculatus;*

*Puccinia* species, such as, for example, *Puccinia recondita;*

*Sclerotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae*; and

*Pseudocercosporella* species, such as, for example, *Pseudocercosporella herpotrichoides.*

The active compounds according to the invention also exhibit a potent strengthening effect in plants. They are therefore suitable for mobilizing the plants' intrinsic defences against attack by undesired microorganisms.

Plant-strengthening (resistance-inducing) substances are to be understood as meaning, in the present context, those substances which are capable of stimulating the defence system of plants in such a way that the treated plants, when subsequently inoculated with undesired microorganisms, develop a high degree of resistance to these microorganisms.

Undesired microorganisms are understood as meaning, in the present case, phytopathogenic fungi, bacteria and viruses. The substances according to the invention can thus be employed to protect plants against infection by the abovementioned pathogens within a specific period post-treatment. The period within which protection is brought about generally extends from 1 to 10 days, preferably 1 to 7 days, after the treatment of the plants with the active compounds.

The fact that the active compounds are well tolerated by plants at the concentrations required for controlling plant diseases permits the treatment of aerial plant parts, of propagation stock and seeds, and of the soil.

The active compounds according to the invention are also suitable for increasing the yield. Moreover, they have a low degree of toxicity and are well tolerated by plants.

If appropriate, the active compounds according to the invention can also be employed in specific concentrations and application rates as herbicides, for influencing plant growth, and for controlling animal pests. If appropriate, they may also be employed as intermediates and precursors for the synthesis of further active compounds.

In the protection of materials, the substances according to the invention can be employed for protecting industrial materials against infection with, and destruction by, undesired microorganisms.

Industrial materials in the present context are understood as meaning non-live materials which have been prepared for use in industry. For example, industrial materials which are intended to be protected by active compounds according to the invention from microbial change or destruction can be glues, sizers, paper and board, textiles, leather, wood, paints and synthetic articles, cooling lubricants and other materials which can be infected with, or destroyed by, microorganisms. Parts of production plants, for example cooling-water circuits, which may be impaired by the multiplication of microorganisms, may also be mentioned within the scope of the materials to be protected. Industrial materials which may be mentioned within the scope of the present invention are preferably glues, sizers, paper and board, leather, wood, paints, cooling lubricants and heat-transfer liquids, especially preferably wood.

Microorganisms which may bring about degradation of, or change in, the industrial materials, and which may be mentioned are, for example, bacteria, fungi, yeasts, algae and slime organisms. The active compounds according to the invention preferably act against fungi, in particular moulds, wood-discolouring and wood-destroying fungi (*Basidiomycetes*), and against slime organisms and algae.

Microorganisms of the following genera may be mentioned by way of example:

*Alternaria,* such as *Alternaria tenuis,*

*Aspergillus,* such as *Aspergillus niger,*

*Chaetomium,* such as *Chaetomium globosum,*

*Coniophora,* such as *Coniophora puetana,*

*Lentinus,* such as *Lentinus tigrinus,*

*Penicillium,* such as *Penicillium glaucum,*

*Polyporus,* such as *Polyporus versicolor,*

*Aureobasidium,* such as *Aureobasidium pullulans,*

*Sclerophoma,* such as *Sclerophoma pityophila,*

*Trichoderma,* such as *Trichoderma viride,*

*Escherichia,* such as *Escherichia coli,*

*Pseudomonas,* such as *Pseudomonas aeruginosa,*

*Staphylococcus,* such as *Staphylococcus aureus.*

Depending on their particular physical and/or chemical properties, the active compounds can be converted into the customary formulations, such as solutions, emulsions, suspensions, powders, foams, pastes, granules, aerosols, microencapsulations in polymeric substances and in coating compositions for seed, and also ULV cold- and warm-fogging products.

These formulations are produced in a known manner, for example by mixing the active compounds with extenders, that is liquid solvents, pressurized liquified gases and/or solid carriers, optionally with the use of surfactants, that is emulsifiers and/or dispersants and/or foam-formers. If water is used as an extender, organic solvents can, for example, also be used as cosolvents. Liquid solvents which are mainly suitable are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water. Liquified gaseous extenders or carriers are those liquids which are gaseous at normal temperature and under atmospheric pressure, for example aerosol propellents such as halogenohydrocarbons and also butane, propane, nitrogen and carbon dioxide. Solid carriers which are suitable are: for example, ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example, crushed and fractionated natural rocks such as calcite, marble, pumice, sepiolite and dolomite, and synthetic granules of inorganic and organic meals, and granules of organic material such as sawdust, coconut shells, maize cobs and tobacco stalks. Suitable emulsifiers and/or foam formers are: for example, non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. Suitable dispersants are: for example, lignin-sulphite waste liquors and methylcellulose.

Adhesives such as carboxymethylcellulose and natural and synthetic polymers in the form of powders, granules or latices such as gum arabic, polyvinyl alcohol and polyvinyl acetate, and natural phospholipids such as cephalins and lecithins, and synthetic phospholipids can be used in the formulations. Further additives can be mineral and vegetable oils.

It is possible to use colourants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention may be present, as such or in their formulations, in a mixture with known fungicides, bactericides, acaridices, nematicides, or insecticides, for example to widen the spectrum of action or to prevent the build-up of resistance. In many cases, synergistic effects result, i.e. the activity of the mixture exceeds the activity of the individual components.

Examples of suitable components in mixtures are the following compounds:

Fungicides aldimorph, ampropylfos, ampropylfos-potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvone, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezin, dicloran, diethofencarb, difenoconazole, dimethirimol, dimethomorph, diniconazole, diniconazole-M, dinocap, diphenylamin, dipyrithione, ditalimfos, dithianon, dodemorph, dodine, drazoxolon, ediphenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxyde, ferbam, ferimzone, fluazinam, flumetover, fluoromid, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazol, imazalil, imibenconazole, iminoctadine, iminoctadine albesilate, iminoctadine triacetate, iodocarb, ipconazole, iprobenfos (IBP), iprodione, irumamycin, isoprothiolan, isovaledione, kasugamycin, kresoxim-methyl, copper preparations such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiine, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamid, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-b-propyl-1H-1,2,4-triazole-1-ethanol,

α-(2,4-dichlorophenyl)-β-methoxy-a-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-a-(methoxyimino)-N-methyl-2-phenoxy-phenylacetamide, 1-isopropyl {2-methyl-1-[[[1-(4-methylphenyl)-ethyl]-amino]-carbonyl]-propyl}-carbonate 1-(2,4-dichlorophenyl)-2-(1H-1,2,4-triazol-1-yl)-ethanone O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]-4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2, 4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole,
2-[[6-deoxy-4-O-(4-O-methyl-β-D-glycopyranosyl)-a-D-glucopyranosyl]-amino]4-methoxy-1H-pyrrolo[2,3-d]pyrimidine-5-carbonitrile,
2-aminobutane,
2-bromo-2-(brommethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol(OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinolin sulphate, 9H-xanthene-9-carboxylic acid 2-[(phenylamino)-carbonyl]-hydrazide,
bis-(1-methylethyl)-3-methyl-4-[(3-methylbenzoyl)-oxy]-2,5-thiophene dicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride, Ethyl [(4-chlorophenyl)-azo]-cyanoacetate, potassium hydrogen carbonate,
Sodium methane tetrathiolate,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxymethanimidamide,
sodium N-formyl-N-hydroxy-DL-alaninate,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothibate,
spiro[2H]-1-benzopyran-2,1'(3'H)-isobenzofuran]-3'-one,
4-[3,4-dimethoxyphenyl)-3-(4-fluorophenyl)-acryloyl]-morpholine.

Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, Baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoate, dimethylvinphos, diofenolan, disulfoton, docusate-sodium, dofenapyn, eflusilanate, emamectin, empenthrin, endosulfan, *Entomophthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses halofenozide, HCH, heptenophos, hexaflumuron, hexythiazox, hydroprene, imidacloprid, indoxacarb, isazofos, isofenphos, isoxathion, ivermectin, nuclear polyhedrosis viruses lambda-cyhalothrin, lufenuron malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron
ometboate, oxamyl, oxydemethon M

*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos, ribavirin salithion, sebufos, silafluofen, spinosad, spirodiclofen, sulfotep, suiprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii* YI 5302 zeta-cypermethrin, zolaprofos (1R-cis)-[5-(phenylmethyl)-3-furanyl]-methyl-3-[(dihydro-2-oxo-3(2H)-furanylidene)-methyl]2,2-dimethylcyclopropanecarboxylate (3-phenoxyphenyl)-methyl 2,2,3,3-tetramethylcyclopropanecarboxylate 1-[(2-chloro-5-thiazolyl)methyl]tetrahydro-3,5-dimethyl-N-nitro-1,3,5-triazin-2(1H)-imine 2-(2-chloro-6-fluorophenyl)-4-[4-(1,1-dimethylethyl)phenyl]-4,5-dihydro-oxazole 2-(acetlyoxy)-3-dodecyl-1,4-naphthalenedione, 2-chloro-N-[[[4-(1-phenylethoxy)-phenyl]-amino]-carbonyl]-benzamide 2-chloro-N-[[[4-(2,2-dichloro-1,1-difluorethoxy)-phenyl]-amino]-carbonyl]-benzamide 3-methylphenyl propylcarbamate 4-[4-(4-ethoxyphenyl)-4-methylpentyl]-1-fluoro-2-phenoxy-benzene 4-chloro-2-(1,1-dimethylethyl)-5-[[2-(2,6-dimethyl-4-phenoxyphenoxy)ethyl]thio]-3(2H)-pyridazinone 4-chloro-2-(2-chloro-2-methylpropyl)-5-[(6-iodo-3-pyridinyl)methoxy]-3(2H)-pyridazinone 4-chloro-5-[(6-chloro-3-pyridinyl)methoxy]-2-(3,4-dichlorphenyl)-3(2H)-pyridazinone

*Bacillus thuringiensis* strain: EG-2348

[2-benzoyl-1-(1,1-dimethylethyl)]-benzohydrazide 2,2-dimethyl-3-(2,4-dichlorophenyl)-2-oxo-1-oxaspiro[4.5]dec-3-en-4-yl-ester butanoate

[3-[(6-chloro-3-pyridinyl)methyl]-2-thiazolidinylidene]-cyanamide dihydro-2-(nitromethylene)-2H-1,3-thiazine-3(4H)-carboxaldehyde ethyl [2-[[1,6-dibydro-6-oxo-1-(phenylmethyl)-4-pyridazinyl]oxy]ethyl]-carbamate N-(3,4,4-trifluoro-1-oxo-3-butenyl)-glycine N-(4-chlorophenyl)-3-[4-(difluoromethoxy)phenyl]-4,5-dihydro-4-phenyl-1H-pyrazole-1-carboxamide N-[(2-chloro-5-thiazolyl)methyl]-N'-methyl-N''-nitro-guanidine N-methyl-N'-(1-methyl-2-propenyl)-1,2-hydrazine dicarbothioamide N-methyl-N'-2-propenyl-1,2-hydrazine dicarbothioamide O,O-diethyl [2-(dipropylamino)-2-oxoethyl]-ethylphosphoramidothioate N-cyanomethyl-4-trifluoromethyl-nicotinamide 3,5-dichloro-1-(3,3-dichloro-2-propenyloxy)-4-[3-(5-trifluoromethylpyridin-2-yloxy)-propoxy]-benzene A mixture with other known active compounds such as herbicides or with fertilizers and growth regulators is also possible.

In addition, the compounds of the formula (I) according to the invention also exhibit very good antimycotic actions. They have a very broad antimycotic spectrum of action, in particular against dermatophytes and yeasts, moulds and diphasic fungi (for example against *Candida* species such as *Candida albicans, Candida glabrata*) and also *Epidermophyton floccosum, Aspergillus* species such as *Aspergillus niger* and *Aspergillus fumigatus, Trichophyton* species such as *Trichophyton mentagrophytes.*

*Microsporon* species such as *Microsporon canis* and audouinii. The elimination of these fungi constitutes in no way a limitation of the mycotic spectrum which can be controlled, but has merely illustrative character.

The active compounds can be used as such, in the form of their formulations or the use forms prepared therefrom, such as ready-to-use solutions, suspensions, wettable powders, pastes, soluble powders, dusts and granules. They are applied in the customary fashion, for example by pouring, spraying, atomizing, spreading, dusting, foaming, brushing on and the like. It is furthermore possible to apply the active compounds by the ultra-low-volume method or to inject the active compound preparation, or the active compound itself, into the soil. The seed of the plants may also be treated.

When employing the active compounds according to the invention as fungicides, the application rates can be varied within a substantial range, depending on the type of application. When treating plant parts, the application rates of active compounds are generally between 0.1 and 10 000 g/ha, preferably between 10 and 1000 g/ha. In the treatment of seed, the application rates of active compound are generally between 0.001 and 50 g per kilogram of seed, preferably between 0.01 and 10 g per kilogram of seed. In the treatment of the soil, the application rates of active compound are generally between 0.1 and 10 000 g/ha, preferably between 1 and 5 000 g/ha.

The preparation and the use of the active compounds according to the invention can be seen from the examples which follow.

PREPARATION EXAMPLES

Example I-1-a-1

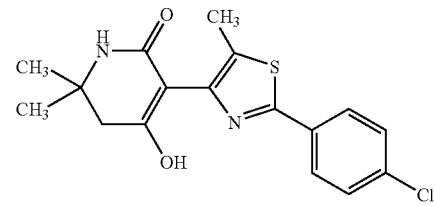

13.8 g of the compound of Example (II-1) in 28 ml of absolute DMF are added dropwise at 0–10° C. to 8.95 g (0.075 mol) of potassium tert-butoxide in 23 ml of absolute dimethylformamide (DMF).

The mixture is stired at 20° C. until the reaction has ended (check by thin-layer chromatography (TLC)).

250 ml of ice-water are added, the mixture is acidified at 0–10° C. with concentrated hydrochloric acid to pH 2 and filtered with suction. This is followed by washing with ice-water, drying and boiling up in methyl tert-butyl ether (MTBE)/n-hexane.

This is followed by purification by column chromatography on silica gel (dichloromethane/acetone, 5:1).

Yield: 10.58 g (86% of theory)

The following compounds of the formula (I-1-a) are obtained analogously to Example (I-1-a-1) and following the general preparation instructions:

(I-1-a)

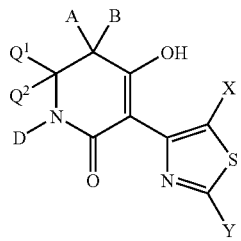

| Ex. No. | X | Y | A | B | D | Q¹ | Q² | M.p. °C. |
|---|---|---|---|---|---|---|---|---|
| I-1-a-2 | $CH_3$ | 4-Cl—$C_6H_4$ | H | H |  | —$(CH_2)_4$— | H | 141 |
| I-1-a-3 | $CH_3$ | 4-Cl—$C_6H_4$ | —$(CH_2)_2$—O—$(CH_2)_2$— | | H | H | H | |
| I-1-a-4 | $CH_3$ | 4-Cl—$C_6H_4$ | H | H | H | —$(CH_2)_2$—O—$(CH_2)_2$— | | 236 |
| I-1-a-5 | Cl | 4-Cl—$C_6H_4$ | H | H | H | $CH_3$ | $CH_3$ | 183 |
| I-1-a-6 | $CH_3$ | 4-Cl—$C_6H_4$ | H | H | ▷— | $CH_3$ | $CH_3$ | 165 |
| I-1-a-7 | $CH_3$ | 4-$CF_3$—$C_6H_4$ | H | H | H | $CH_3$ | $CH_3$ | 181 |
| I-1-a-8 | $CH_3$ | 3-Cl—$C_6H_4$ | H | H | $CH_3$ | $CH_3$ | | 173 |
| I-1-a-9 | $CH_3$ | 2-Cl-4-$OC_2H_5$—$C_6H_3$ | H | H | H | $CH_3$ | $CH_3$ | 212 |
| I-1-a-10 | $CH_3$ | 4-$CH_3$—$C_6H_4$ | H | H | H | $CH_3$ | $CH_3$ | 209 |
| I-1-a-11 | $C_2H_5$ | 4-Cl—$C_6H_4$ | H | H | H | $CH_3$ | $CH_3$ | 210 |
| I-1-a-12 | $C_3H_7$ | 4-Cl—$C_6H_4$ | H | H | H | $CH_3$ | $CH_3$ | 215 |
| I-1-a-13 | $CH_3$ | 4-Cl—$C_6H_4$ | $CH_3$ | $CH_3$ | H | $CH_3$ | $CH_3$ | 254 |
| I-1-a-14 | Cl | 4-Cl—$C_6H_4$ | $CH_3$ | $CH_3$ | H | $CH_3$ | $CH_3$ | |

Example I-1-b-1

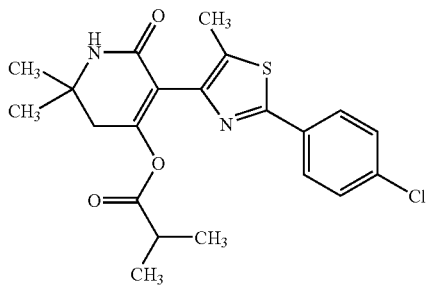

1.05 g of the compound of Ex. I-1-a-1 are introduced into 30 ml of anhydrous ethyl acetate and treated with 0.46 ml (3.3 mmol) of triethylamine. 0.34 ml (0.0033 mol) of isobutyrol chloride in 5 ml of anhydrous ethyl acetate is added dropwise under reflux, and stirring is continued under reflux until the reaction has ended (check by thin-layer chromatography). The solvent is distilled off in vacuo and the residue is taken up in dichloromethane. This is washed 2× with 20 ml of 0.5 N NaOH solution and dried, and the solvent is evaporated.

This is followed by purification by column chromatography over silica gel (dichloromethane/ethyl acetate 3:1) Yield: 0.57 g (45% of theory), M.p.: 189° C.

The following compounds of the formula I-1-b are obtained analogously to Example I-1-b-1 and following the general preparation instructions:

(I-1-b)

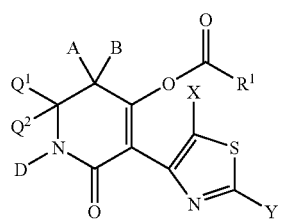

| Ex. No. | X | Y | A | B | D | Q¹ | Q² | R¹ | M.p. °C. |
|---|---|---|---|---|---|---|---|---|---|
| I-1-b-2 | $CH_3$ | 4-Cl—$C_6H_4$ | H | H | H | $CH_3$ | $CH_3$ | Cl—C₆H₄— | 229 |

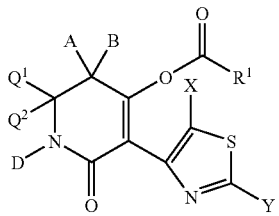
(I-1-b)

| Ex. No. | X | Y | A | B | D | Q¹ | Q² | R¹ | M.p. °C. |
|---|---|---|---|---|---|---|---|---|---|
| I-1-b-3 | $CH_3$ | 4-Cl—$C_6H_4$ | H | H | H | $CH_3$ | $CH_3$ | 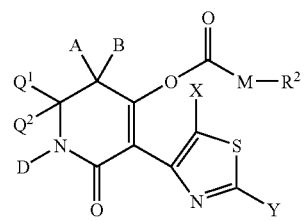 | 213 |
| I-1-b-4 | $CH_3$ | 4-Cl—$C_6H_4$ | H | H | H | $CH_3$ | $CH_3$ | $C_2H_5O$—$CH_2$— | 168 |

Example I-1-c-1

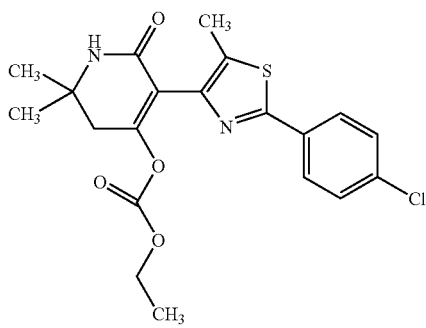

0.1 ml (1 mmol) of ethyl chloroformate in 1 ml of absolute dichloromethane are added at 10–20° C. to 0.35 g of the compound of Example (I-1-a-1) in 11 ml of absolute dichloromethane and 0.1 ml (1 mmol) of triethylamine.

The mixture is stirred at room temperature until the reaction has ended (TLC check) and the solvent is evaporated on a rotary evaporator. The precipitate is taken up in dichloromethane and the mixture is washed twice with 5 ml of 0.5 N sodium hydroxide solution, dried and concentrated.

This is followed by purification by column chromatography on silica gel (dichloromethane/ethyl acetate 5:1).

Yield: 0.17 g (40% of theory)

The following compounds of the formula (I-1-c) are obtained analogously to Example (I-1-c-1) and following the general preparation instructions (I-1-c)

| Ex. No. | X | Y | A | B | D | Q¹ | Q² | M | R² | M.p. °C. |
|---|---|---|---|---|---|---|---|---|---|---|
| I-1-c-2 | $CH_3$ | 4-Cl—$C_6H_4$ | H | H | H | $CH_3$ | $CH_3$ | O | phenyl | 210 |

(I-1-c)

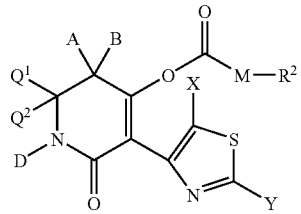

| Ex. No. | X | Y | A | B | D | Q¹ | Q² | M | R² | M.p. °C |
|---|---|---|---|---|---|---|---|---|---|---|
| I-1-c-3 | $CH_3$ | 4-Cl—$C_6H_4$ | H | H | H | $CH_3$ | $CH_3$ | O | 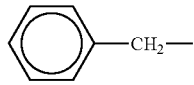 | 209 |
| I-1-c-4 | $CH_3$ | 4-Cl—$C_6H_4$ | H | H | H | $CH_3$ | $CH_3$ | S | 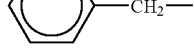 | 198 |

Ex. No. I-1-g-1

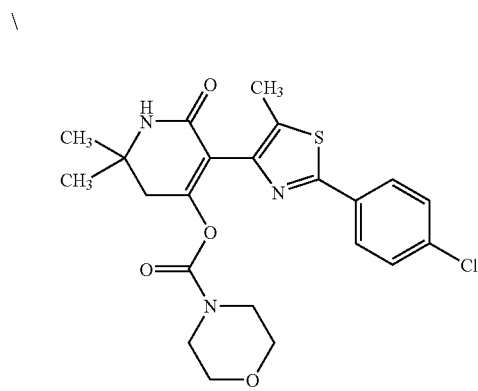

1.05 g of the compound of Example I-1-a-1 are introduced into 10 ml of anhydrous ethyl acetate, and 0.42 ml (3 mmol) of triethylamine were added. 0.4 ml (0.0033 mol) of morpholinocarbamoyl chloride in 2 ml of anhydrous ethyl acetate are added dropwise under reflux, and stirring is continued under reflux until the reaction has ended (check by thin-layer chromatography). The solvent is distilled off and the residue is taken up in dichloromethane. The mixture is washed 2× with 20 ml of 0.5 N NaOH solution and dried, and the solvent is evaporated.

This is followed by purification by column chromatography over silica gel (dichloromethane/ethyl acetate, 5:1) Yield: 0.22 g (15% of theory), M.p.: 217° C.

Example II-1

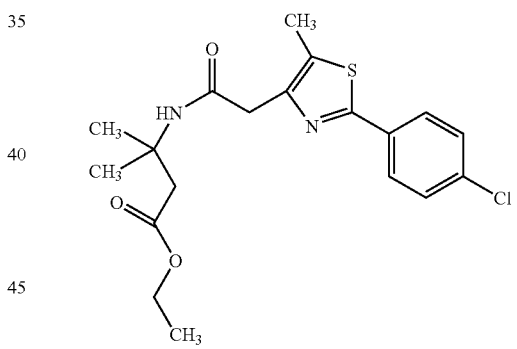

18 g of 5-methyl-2-(4-chloro-phenyl)-thiazolylacetic acid are added to 10 g of ethyl 3-amino-3-methyl-butyrate in 250 ml of absolute tetrahydrofuran and 12 ml of triethylamine, and the mixture is stirred for 15 minutes at room temperature. 13.2 ml of triethylamine are subsequently added, and 3.4 ml of phosphorus oxychloride are immediately added dropwise in such a way that the solution boils moderately.

The mixture is stirred for a further 30 minutes under reflux. Then, the reaction solution is stirred into 800 ml of ice-water and extracted with dichloromethane, and the dichloromethane phase is dried and evaporated. This is followed by purification by column chromatography on silica gel (n-hexane/ethyl acetate, 2:1).

Yield: 13.81 g (52% of theory), M.p. 101° C.

The following compounds of the formula (II) are obtained analogously to Example (II-1) and following the general preparation instructions:

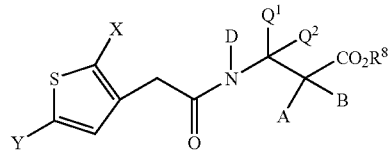

(II)

| Ex. No. | X | Y | A | B | D | Q¹ | Q² | R⁸ | M.p. °C. |
|---|---|---|---|---|---|---|---|---|---|
| II-2 | $CH_3$ | 4-Cl—$C_6H_4$ | H | H | H | —$(CH_2)_4$— | | $C_2H_5$ | oil |
| II-3 | $CH_3$ | 4-Cl—$C_6H_4$ | —$(CH_2)_2$—O—$(CH_2)_2$— | | H | H | H | $C_2H_5$ | 127 |
| II-4 | $CH_3$ | 4-Cl—$C_6H_4$ | H | H | H | —$(CH_2)_2$—O—$(CH_2)_2$— | | $C_2H_5$ | 129 |
| II-5 | Cl | 4-Cl—$C_6H_4$ | H | H | H | $CH_3$ | $CH_3$ | $C_2H_5$ | 115 |
| II-6 | $CH_3$ | 4-Cl—$C_6H_4$ | H | H | cyclopropyl | $CH_3$ | $CH_3$ | $C_2H_5$ | 86 |
| II-7 | $CH_3$ | 4-$CF_3$—$C_6H_4$ | H | H | H | $CH_3$ | $CH_3$ | $C_2H_5$ | 94 |
| II-8 | $CH_3$ | 3-Cl—$C_6H_4$ | H | H | H | $CH_3$ | $CH_3$ | $C_2H_5$ | 89 |
| II-9 | $CH_3$ | 2,4-$Cl_2$—$C_6H_3$ | H | H | H | $CH_3$ | $CH_3$ | $C_2H_5$ | 93 |
| II-10 | $CH_3$ | 4-$CH_3$—$C_6H_4$ | H | H | H | $CH_3$ | $CH_3$ | $C_2H_5$ | 88 |
| II-11 | $C_2H_5$ | 4-Cl—$C_6H_4$ | H | H | H | $CH_3$ | $CH_3$ | $C_2H_5$ | 105 |
| II-12 | $C_3H_7$ | 4-Cl—$C_6H_4$ | H | H | H | $CH_3$ | $CH_3$ | $C_2H_5$ | 69 |
| II-13 | $CH_3$ | 4-Cl—$C_6H_4$ | $CH_3$ | $CH_3$ | H | $CH_3$ | $CH_3$ | $CH_3$ | 144 |
| II-14 | Cl | 4-Cl—$C_6H_4$ | $CH_3$ | $CH_3$ | H | $CH_3$ | $CH_3$ | $CH_3$ | 87 |
| II-15 | Cl | 4-Cl—$C_6H_4$ | $CH_3$ | $CH_3$ | H | H | H | $C_2H_5$ | 99 |
| II-16 | $C_2H_5$ | 4-Cl—$C_6H_5$ | H | H | H | —$(CH_2)_2$—O—$(CH_2)2$)— | | $C_2H_5$ | oil |

Example I-2-a-1

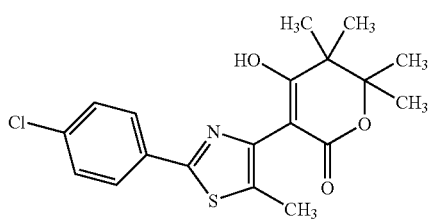

1.5 g of the compound of Example III-1 in 5 ml of absolute acetonitrile are added at room temperature to 0.68 g (6 mmol) of potassium tert-butoxide in 10 ml of absolute acetonitrile.

The mixture is stirred for 3 hours at room temperature. The solution is poured into ice-water, acidified with 1 N hydrochloric acid, filtered off with suction and dried. This is followed by purification by column chromatography on silica gel (n-hexane/ethyl acetate 5:1).

Yield: 0.23 g (16% of theory) M.p. 138–140° C.

The following compounds of the formula (I-2-a) are obtained analogously to Example (I-2-a-1) and following the general preparation instructions:

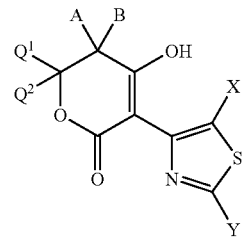

(I-2-a)

| Ex. No. | X | Y | A | B | Q¹ | Q² | M.p. °C. |
|---|---|---|---|---|---|---|---|
| I-2-a-2 | $CH_3$ | 4-Cl—$C_6H_4$ | $CH_3$ | $CH_3$ | H | H | 133 |
| I-2-a-3 | $C_2H_5$ | 4-Cl—$C_6H_4$ | $CH_3$ | $CH_3$ | H | H | 129 |
| I-2-a-4 | $C_2H_5$ | 4-Cl—$C_6H_4$ | $CH_3$ | $CH_3$ | $CH_3$ | $CH_3$ | 144–145 |

Example-No. I-2-b-1

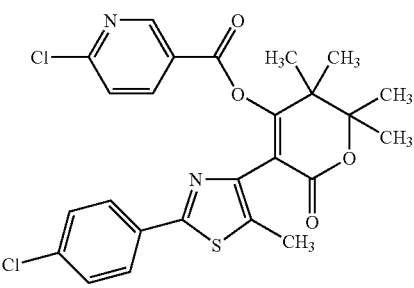

190 mg of the compound of Example I-2-a-1 in 5 ml of anhydrous dichloromethane are treated with 0.105 ml of triethylamine. 115 mg of 6-chloronicotinoyl chloride are added with ice-cooling, and the mixture is stirred at room temperature.

The reaction solution is washed 1× with 10% citric acid solution, the aqueous phase is extracted with dichloromethane, the organic phase is washed 1× with 1 N NaOH, and the aqueous phase is extracted with dichloromethane. This is followed by drying and evaporation of the solvent on a rotary evaporator.

Yield: 0.17 g (65% of theory)

$^1$H NMR (DMSO, 400MHz): δ=1.30, 1.56 (2 s, in each case 6H, 4 CH$_3$) 2.29 (s, 3H, thiazolyl-$\underline{CH_3}$), 7.41, 7.59 (2d, in each case 2H, Ar—H) 7.57 (d, 1H, pyridyl-H), 8.25 (d, 1H, pyridyl-H), 8.83 (s, 1H, pyridyl-H) ppm.

The following compounds of the formula (I-2-b) are obtained analogously to Example (I-2-b-1) and following the general preparation instructions 300 mg (0.8 mmol) of the compound of Example I-2-a-1 in 10 ml of anhydrous dichloromethane are treated with 0.17 ml (1.2 mmol) of triethylamine. 0.1 ml (1.04 mmol) of ethyl chloroformate is subsequently added at 0° C.

The mixture is stirred at room temperature.

The reaction solution is washed 1× with 10% citric acid solution, the aqueous phase is extracted with dichloromethane, the organic phase is washed 1× with 1 N NaOH, and the aqueous phase is extracted with dichloromethane. This is followed by drying and evaporation of the solvent on a rotary evaporator.

Yield: 0.3 g (83% of theory).

(I-2-b)

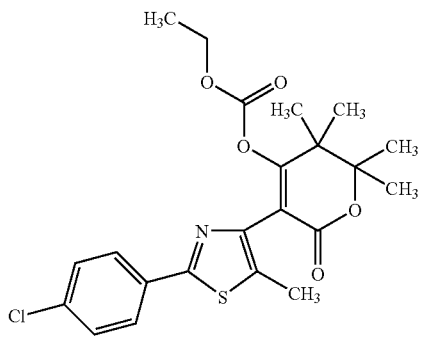

| Ex. No | X | Y | A | B | Q$^1$ | Q$^2$ | R$^1$ | M.p. ° C. |
|---|---|---|---|---|---|---|---|---|
| I-2-b-2 | CH$_3$ | 4-Cl—C$_6$H$_4$ | CH$_3$ | CH$_3$ | H | H | i-C$_4$H$_9$ | oil |
| I-2-b-3 | C$_2$H$_5$ | 4-Cl—C$_6$H$_4$ | CH$_3$ | CH$_3$ | H | H | H$_5$C$_2$—CH$_2$— | oil |

Example-No. 1–2-c-1

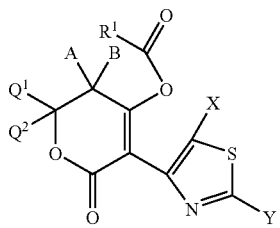

$^1$H NMR (400 MHz, CDCl$_3$): δ=0.94 (t, 3H, $\underline{CH_3}$—CH$_2$—O), 1.22 (s, 6H, 2CH$_3$), 1.48 (s, 6H, 2CH$_3$), 1.27 (s, 3H, CH$_3$), 3.95 (q, $\underline{CH_3}$—CH$_2$—O), 7.56 (d, 2H, arom. CH), 7.83 (d, 2H, arom. CH) ppm.

The following compound of the formula (I-2-c) is obtained analogously to Example (I-2-c-1) and following the general preparation instructions (I-2-c)

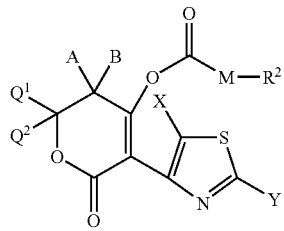

| Ex. No. | X | Y | A | B | Q$^1$ | Q$^2$ | M | R$^2$ | M.p. ° C. |
|---|---|---|---|---|---|---|---|---|---|
| I-2-c-2 | CH$_3$ | 4-Cl—C$_6$H$_4$ | CH$_3$ | CH$_3$ | H | H | O | C$_2$H$_5$ | oil |
| I-2-c-3 | C$_2$H$_5$ | 4-Cl—C$_6$H$_4$ | CH$_3$ | CH$_3$ | H | H | O | C$_2$H$_5$ | oil |

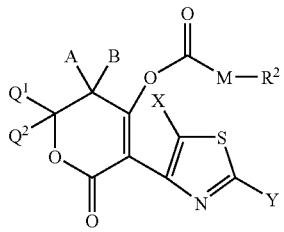

| Ex. No. | X | Y | A | B | Q¹ | Q² | M | R² | M.p. °C. |
|---|---|---|---|---|---|---|---|---|---|
| I-2-c-4 | $C_2H_5$ | 4-Cl—$C_6H_4$ | $CH_3$ | $CH_3$ | H | H | S | (benzyl -CH₂) | oil |

Example III-1

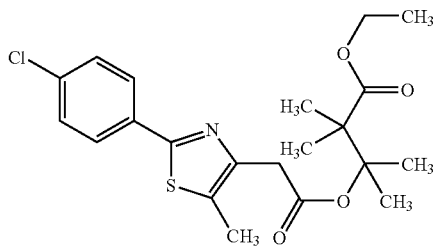

1.6 ml of triethylamine are added to 1.12 g (6.4 mmol) of ethyl 3-hydroxy-2,2,3-trimethyl-butyrate in 20 ml of absolute tetrahydrofuran. The mixture is stirred for 5 minutes, and 1.07 g (4 mmol) of 5-methyl-2-(4-chlorophenyl)-thiazolylacetic acid are added. After a further 15 minutes, 0.9 ml of triethylamine is added, and 0.2 ml of phosphorus oxychloride is immediately added in such a way that the solution boils moderately. The mixture is stirred for 1 hour under reflux. The mixture is concentrated and the product is purified by column chromatography on silica gel (dichloromethane→dichloromethane:ethyl acetate, 3:1).

Yield: 1.5 g (88% of theory)

$^1$H NMR (400 MHz, DMSO): δ=1.11, 1.12 (2 s, in each case 6H, 4-$CH_3$), 1.17 (t, 3H, $\underline{CH_3}$—$CH_2$—O), 2.41 (s, $\underline{CH_3}$-thiazolyl), 7.52, 7.82 (2 d, in each case 2H, aryl-H) ppm.

The following compounds of the formula (III) are obtained analogously to Example (III-1) and following the general preparation instructions:

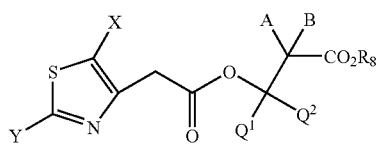

| Ex. No. | X | Y | A | B | Q¹ | Q² | R⁸ | M.p. °C. |
|---|---|---|---|---|---|---|---|---|
| III-2 | $CH_3$ | 4-Cl—$C_6H_4$ | $CH_3$ | $CH_3$ | H | H | $CH_3$ | Oil* |
| III-3 | $C_2H_5$ | 4-Cl—$C_6H_4$ | $CH_3$ | $CH_3$ | H | H | $CH_3$ | Oil* |
| III-4 | $C_2H_5$ | 4-Cl—$C_6H_4$ | $CH_3$ | $CH_3$ | $CH_3$ | $CH_3$ | $C_2H_5$ | Oil* |

Spectroscopic data, Ex. III-4:
$^1$H NMR (400 MHz, DMSO):
δ = 1.04, 1.10, 1.11, 1.50 (4 s, in each case 3 H, 4-$CH_3$), 1.20 (m, 3H, $\underline{CH_3}$—$CH_2$—O), 4.02 (m, 2 H, $CH_3$—$\underline{CH_2}$—O) ppm.
*The oils were converted into the corresponding compounds of the formula 1-2-a without being characterized further.

Use Examples

Example A

*Meloidogyne* Test

| | |
|---|---|
| Solvent: | 30 parts by weight of dimethylformamide |
| Emulsifier: | 1 part by weight of alkylaryl polyglycol ether |

To prepare a suitable active compound preparation, 1 part by weight of active compound is mixed with the stated amounts of solvent and emulsifier and the concentrate is diluted to the desired concentration with water.

Containers are filled with sand, active compound solution, *Meloidogyne incognita* egg/larval suspension and lettuce seeds. The lettuce seeds germinate and the plantlets develop. The galls develop on the roots.

After the desired time, the nematicidal efficacy is determined in % with reference to gall formation. 100% means that no galls were found; 0% means that the number of galls on the treated plants corresponds to that of the untreated control.

In this test, a destruction rate of 100% is shown, for example, by the compounds of Preparation Examples I-1-c-1 and I-2-a-1 at an active compound concentration of 20 ppm, and a destruction rate of 98% after 14 days by the compound of Preparation Example I-2-a-3 at an active compound concentration of 20 ppm.

Example B

*Myzus* Test

| | |
|---|---|
| Solvent: | 30 parts by weight of dimethylformamide |
| Emulsifier: | 1 part by weight of alkylaryl polyglycol ether |

To prepare a suitable active compound preparation, 1 part by weight of active compound is mixed with the stated amounts of solvent and emulsifier and the concentrate is diluted to the desired concentration with emulsifier-containing water.

Cabbage leaves (*Brassica oleracea*) which are severely infested by the green peach aphid (*Myzus persicae*) are treated by immersing into the active compound preparation of the desired concentration.

After the desired time, the destruction rate is determined in %. 100% means that all of the aphids have been destroyed; 0% means that none of the aphids have been destroyed.

In this test, a destruction rate of 90% was caused, after 6 days, by the compound of Preparation Example I-2-a-1 at an active compound concentration of 500 ppm.

Example C

*Phaedon* Larvae Test

| | |
|---|---|
| Solvent: | 30 parts by weight of dimethylformamide |
| Emulsifier: | 1 part by weight of alkylaryl polyglycol ether |

To prepare a suitable active compound preparation, 1 part by weight of active compound is mixed with the stated amounts of solvent and emulsifier and the concentrate is diluted to the desired concentration with emulsifier-containing water.

Cabbage leaves (*Brassica oleracea*) are treated by immersing in the active compound preparation of the desired concentration and populated with larvae of the mustard beetle (*Phaedon cochleariae*) while the leaves are still moist.

After the desired time, the destruction rate is determined in %. 100% means that all the beetle larvae have been destroyed; 0% means that none of the beetle larvae have been destroyed.

In this test, a destruction rate of 100% is shown, after 7 days, for example by the compounds of Preparation Examples I-1-a-1 and I-2-a-2 at an active compound concentration of 1000 ppm, and a destruction rate of 100% after 7 days by the compound of Preparation Example I-2-a-1 at an active compound concentration of 500 ppm.

Example D

*Plutella* Test/Synthetic Feed

| | |
|---|---|
| Solvent: | 100 parts by weight of acetone |
| Emulsifier: | 1900 parts by weight of methanol |

To prepare a suitable active compound preparation, 1 part by weight of active compound is mixed with the stated amounts of solvent and emulsifier and the concentrate is diluted to the desired concentration with methanol.

A stated amount of active compound preparation of the desired concentration is pipetted onto a standardized amount of synthetic feed. After the methanol has evaporated, a film can lid populated with approx. 100 Plutella eggs is placed into each cavity. The freshly hatched larvae migrate onto the treated synthetic feed.

After the desired time, the destruction rate is determined in %. 100% means that all of the animals have been destroyed; 0% means that none of the animals have been destroyed.

In this test, a destruction rate of 100% is shown, after 7 days, for example by the compound of Preparation Example I-2-a-4 at an active compound concentration of 1000 ppm.

Example E

*Spodoptera frugiperda* Test

| | |
|---|---|
| Solvent: | 30 parts by weight of dimethylformamide |
| Emulsifier: | 1 part by weight of alkylaryl polyglycol ether |

To prepare a suitable active compound preparation, 1 part by weight of active compound is mixed with the stated amounts of solvent and emulsifier and the concentrate is diluted to the desired concentration with emulsifier-containing water.

Cabbage leaves (*Brassica oleracea*) are treated by immersing in the active compound preparation of the desired concentration and populated with larvae of the fall armyworm caterpillars (*Spodoptera frugiperda*) while the leaves are still moist.

After the desired time, the destruction rate is determined in %. 100% means that all the caterpillars have been destroyed; 0% means that none of the caterpillars have been destroyed.

In this test, a destruction rate of 100% is shown, after 7 days, for example by the compounds of Preparation Examples I-2-a-2 at an active compound concentration of 1000 ppm and I-2-a-1 at an active compound concentration of 500 ppm.

Example F

Tetranychus Test (OP Resistant/Immersion Treatment)

| Solvent: | 30 parts by weight of dimethylformamide |
|---|---|
| Emulsifier: | 1 part by weight of alkylaryl polyglycol ether |

To prepare a suitable active compound preparation, 1 part by weight of active compound is mixed with the stated amounts of solvent and emulsifier and the concentrate is diluted to the desired concentration with emulsifier-containing water.

Bean plants (Phaseolus vulgaris) which are severely infested by all stages of the two-spotted spider mite (Tetranychus urticae) are immersed into an active compound preparation of the desired concentration.

After the desired time, the efficacy is determined in %. 100% means that all of the spider mites have been destroyed; 0% means that none of the spider mites have been destroyed.

In this test, destruction rates of 100% (Example I-2-a-1), 99% (Example I-2-a-2), 98% (Example I-1-a-1) and 90% (Examples I-2-a-3 and I-2-a-4), respectively, are shown by the compounds of Preparation Examples I-1-a-1, I-2-a-2, I-2-a-3, I-2-a-1 and I-2-a-4 at an active compound composition of 100 ppm.

Example G

Post-emergence Test

| Solvent: | 5 parts by weight of acetone |
|---|---|
| Emulsifier: | 1 part by weight of alkylaryl polyglycol ether |

To prepare a suitable active compound preparation, 1 part by weight of active compound is mixed with the stated amount of solvent, the stated amount of emulsifier is added, and the concentrate is diluted with water to the desired concentration.

Test plants which have a height of 5 to 15 cm are sprayed with the active compound preparation in such a way that the active compound quantities desired in each case are applied per unit area. The concentration of the spray mixture is chosen such that the active compound quantities desired in each case are applied in 1000 l of water/ha.

After three weeks, the degree of damage to the plants is scored in % damage in comparison with the development of the untreated control.

The figures denote:

0%=no effect (like untreated control)

100%=total destruction

Example H

Pre-emergence Test

| Solvent: | 5 parts by weight of acetone |
|---|---|
| Emulsifier: | 1 part by weight of alkylaryl polyglycol ether |

To prepare a suitable active compound preparation, 1 part by weight of active compound is mixed with the stated amount of solvent, the stated amount of emulsifier is added, and the concentrate is diluted with water to the desired concentration.

Seeds of the test plants are sown in normal soil. After approximately 24 hours, the soil is sprayed with the active compound preparation in such a way that the active compound quantities desired in each case are applied per unit area. The concentration of the spray mixture is chosen such that the active compound quantities desired in each case are applied in 1000 l of water/ha.

After three weeks, the degree of damage to the plants is scored in % damage in comparison with the development of the untreated control.

The figures denote:

0%=no effect (like untreated control)

100%=total destruction

| pre-emergence | g ai/ga | Sugar beet | Digitaria | Lolium | Setaria | Matricaria | |
|---|---|---|---|---|---|---|---|
| Ex. I-2-a-1 | 125 | 0 | 100 | 100 | 100 | 95 | |
| post-emergence | g ai/ha | Wheat | Sugar beet | Alopecurus | Avena fatua | Digitaria | Setaria |
| Ex. I-2-a-1 | 125 | 10 | 0 | 90 | 90 | 95 | 100 |
| pre-emergence | g ai/ha | Sugar beet | Avena fatua | Lolium | Setaria | Matricaria | Solanum |
| Ex. I-2-a-4 | 125 | 0 | 95 | 100 | 100 | 100 | 95 |
| post-emergence | g ai/ha | Sugar beet | Avena fatua | Digitaria | Lolium | Setaria | |

| Ex. I-2-a-4 | 125 | 0 | 95 | 100 | 100 | 100 |

Example I

Limit Concentration Test/Soil-dwelling Insects—Treatment of Transgenic Plants

| | |
|---|---|
| Test insect: | *Diabrotica balteata* larvae in the soil |
| Solvent: | 7 parts by weight of acetone |
| Emulsifier: | 1 part by weight of alkylaryl polyglycol ether |

To prepare a suitable active compound preparation, 1 part by weight of active compound is mixed with the stated amount of solvent, the stated amount of emulsifier is added, and the concentrate is diluted with water to the desired concentration.

The active compound preparation is poured onto the soil. The concentration of the active compound in the preparation is of virtually no importance, only the weight of active substance per unit volume of soil, which is indicated in ppm (mg/l), being decisive. The soil is filled into 0.25 l pots, and these are left to stand at 20° C.

Immediately after the test is set up, 5 pregerminated maize kernels cv. YIELD GUARD (trademark of Monsanto Comp., USA) are placed into each pot. The appropriate test insects are put in to the heated soil after 2 days. After a further 7 days, the efficacy of the active compound is determined by counting the maize plants which have emerged (1 plant=20% action).

Example J

*Heliothis* Virescens Test—Treatment of Transgenic Plants

| | |
|---|---|
| Solvent: | 7 parts by weight of acetone |
| Emulsifier: | 1 part by weight of alkylaryl polyglycol ether |

To prepare a suitable active compound preparation, 1 part by weight of active compound is mixed with the stated amount of solvent, the stated amount of emulsifier is added, and the concentrate is diluted with water to the desired concentration.

Sojabean shoots (*Glycine max*) cv. Roundup Ready (trademark of Monsanto Comp. USA) are treated by immersing into the active compound preparation of the desired concentration and populated with the tobacco budworm *Heliothis virescens* while the leaves are still moist.

The destruction of the insects is determined after the desired time.

The invention claimed is:

1. Compounds of the formula (I)

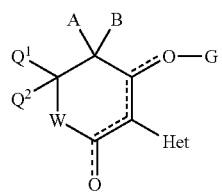

in which

Het represents

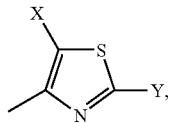

W represents oxygen

X represents hydrogen or $C_1$–$C_6$-alkyl,

Y represents halogen, $C_1$–$C_6$-alkyl, $C_1$–$C_6$-halogenoalkyl, $C_1$–$C_6$-alkoxy, $C_1$–$C_6$-halogenoalkoxy, or a group

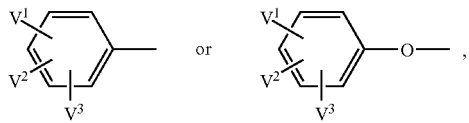

in which $V^1$ represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-halogeno-alkyl, $C_1$–$C_4$-halogenoalkoxy, nitro, cyano, or represents phenyl, phenoxy, phenoxy-$C_1$–$C_4$-alkyl, phenyl-$C_1$–$C_4$-alkoxy, phenylthio-$C_1$–$C_4$-alkyl, or phenyl-$C_1$–$C_4$-alkylthio, each of which is optionally monosubstituted or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro, or cyano, and $V^2$ and $V^3$ independently of one another represent hydrogen, halogen, $C_1$–$C_6$-alkyl, $C_1$–$C_6$-alkoxy, $C_1$–$C_4$-halogenoalkyl, or $C_1$–$C_4$-halogenoalkoxy, or $V^1$ and $V^2$ together with the carbon atoms to which they are bonded represent a 5- or 6-membered cycle that is optionally substituted by $C_1$–$C_4$-alkyl or halogen and in which one to three carbon atoms is optionally replaced by oxygen, sulphur, or nitrogen, A represents hydrogen; optionally halogen-substituted alkyl, alkenyl, alkoxyalkyl, polyalkoxyalkyl, or alkylthioalkyl; optionally substituted saturated or unsaturated cycloalkyl in which one or more ring atoms is optionally replaced by a hetero atom; or aryl, arylalkyl or hetaryl, each of which is optionally substituted by halogen, alkyl, halogenoalkyl, alkoxy, halogenoalkoxy, cyano, or nitro, B represents hydrogen or alkyl, or A and B together with the carbon atom to which they are bonded represent a saturated or unsaturated, unsubstituted or substituted cycle that optionally contains at least one hetero atom;

$Q^1$ represents hydrogen; alkyl; alkoxyalkyl; optionally substituted cycloalkyl in which one methylene group is optionally replaced by oxygen or sulphur; or optionally substituted phenyl, $Q^2$ represents hydrogen or alkyl, or $Q^1$ and $Q^2$ together with the carbon atom to which they are bonded represent an unsubstituted or substituted cycle that optionally contains one hetero atom, and G represents hydrogen (a) or one of the groups

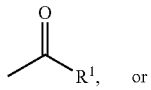   or

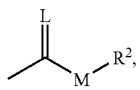

in which

L represents oxygen or sulphur,

M represents oxygen or sulphur, $R^1$ represents optionally halogen-substituted alkyl, alkenyl, alkoxyalkyl, alkylthioalkyl, or polyalkoxyalkyl; cycloalkyl that is optionally substituted by halogen, alkyl, or alkoxy and that is optionally interrupted by one or more hetero atoms; or optionally substituted phenyl, phenylalkyl, hetaryl, phenoxyalkyl, or hetaryloxyalkyl, and $R^2$ represents optionally halogen-substituted alkyl, alkenyl, alkoxyalkyl, or polyalkoxyalkyl; or optionally substituted cycloalkyl, phenyl, or benzyl.

2. A Compound of formula (I) according to claim 1 in which

Het represents

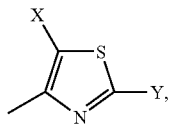

W represents oxygen,

X represents hydrogen or $C_1$–$C_6$-alkyl,

Y represents halogen, $C_1$–$C_6$-alkyl, $C_1$–$C_6$-halogenoalkyl, $C_1$–$C_6$-alkoxy, $C_1$–$C_6$-halogenoalkoxy, or a group

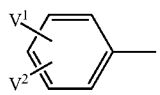   or   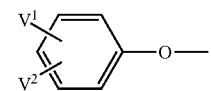

in which $V^1$ represents hydrogen, halogen, $C_1$–$C_{12}$-alkyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_4$-halogenoalkyl, $C_1$–$C_4$-halogenoalkoxy, nitro, cyano, or represents phenyl, phenoxy, phenoxy-$C_1$–$C_4$-alkyl, phenyl-$C_1$–$C_4$-alkoxy, phenylthio-$C_1$–$C_4$-alkyl or phenyl-$C_1$–$C_4$-alkylthio, each of which is optionally monosubstituted or polysubstituted by halogen, $C_1$–$C_6$-alkyl, $C_1$–$C_6$-alkoxy, $C_1$–$C_4$-halogenoalkyl, $C_1$–$C_4$-halogenoalkoxy, nitro, or cyano, and $V^2$ and $V^3$ independently of one another represent hydrogen, halogen, $C_1$–$C_6$-alkyl, $C_1$–$C_6$-alkoxy, $C_1$–$C_4$-halogenoalkyl, or $C_1$–$C_4$-halogenoalkoxy, or $V^1$ and $V^2$ together with the carbon atoms to which they are bonded represent a 5- or 6-membered cycle which is optionally substituted by $C_1$–$C_4$-alkyl or halogen and in which one to three carbon atoms is optionally replaced by oxygen, sulphur or nitrogen, A represents hydrogen; $C_1$–$C_{12}$-alkyl, $C_3$–$C_8$-alkenyl, or $C_1$–$C_6$-alkoxy-$C_1$–$C_4$-alkyl, each of which is optionally substituted by halogen; optionally halogen-, $C_1$–$C_4$-alkyl-, or $C_1$–$C_4$-alkoxy-substituted $C_3$–$C_8$-cycloalkyl, or $C_3$–$C_6$-cyclo-alkyl-$C_1$–$C_4$-alkyl in which one or two ring members that are not directly adjacent are optionally replaced by oxygen and/or sulphur; or phenyl, benzyl, hetaryl having 5 to 6 ring atoms, or hetaryl-$C_1$–$C_4$-alkyl having 5 to 6 ring atoms each of which phenyl, benzyl, hetaryl, or hetaryl-$C_1$–$C_4$-alkyl group is optionally substituted by halogen, $C_1$–$C_6$-alkyl, $C_1$–$C_6$-halogenoalkyl, $C_1$–$C_6$-alkoxy, $C_1$–$C_6$-halogenoalkoxy, cyano, or nitro, B represents hydrogen or $C_1$–$C_6$-alkyl, or A, B, and the carbon atom to which they are bonded represent saturated $C_3$–$C_{10}$-cycloalkyl or unsaturated $C_5$–$C_{10}$-cycloalkyl in which one ring member is optionally replaced by oxygen or sulphur and that are optionally mono-substituted or disubstituted by $C_1$–$C_6$-alkyl, $C_3$–$C_8$-cycloalkyl, $C_1$–$C_6$-halogenoalkyl, $C_1$–$C_6$-alkoxy, $C_1$–$C_6$-alkylthio, halogen, or phenyl, $Q^1$ represents hydrogen; $C_1$–$C_6$-alkyl; $C_1$–$C_6$-alkoxy-$C_1$–$C_2$-alkyl; $C_3$–$C_8$-cycloalkyl in which one methylene group is optionally replaced by oxygen or sulphur and that is optionally substituted by fluorine, chlorine, $C_1$–$C_4$-alkyl, $C_1$–$C_2$-halogenoalkyl, or $C_1$–$C_4$-alkoxy; or phenyl that is optionally substituted by halogen, $C_1$–$C_4$-alkyl, $C_1$–$C_4$-alkoxy, $C_1$–$C_2$-halogenoalkyl, $C_1$–$C_2$-halogeno-alkoxy, cyano, or nitro, $Q^2$ represents hydrogen or $C_1$–$C_4$-alkyl, or $Q^1$ and $Q^2$ together with the carbon atom to which they are bonded represent $C_3$–$C_7$-cycloalkyl in which one ring member is optionally replaced by oxygen or sulphur and that is optionally substituted by $C_1$–$C_6$-alkyl, $C_1$–$C_6$-alkoxy, or $C_1$–$C_2$-halogenoalkyl, and G represents hydrogen (a) or one of the groups

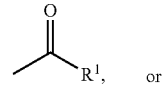   or

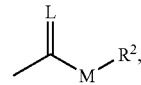

in which

L represents oxygen or sulphur,

M represents oxygen or sulphur, $R^1$ represents $C_1$–$C_{20}$-alkyl, $C_1$–$C_{20}$-alkenyl, $C_1$–$C_8$-alkoxy-$C_1$–$C_8$-alkyl, $C_1$–$C_8$-alkylthio-$C_1$–$C_8$-alkyl, or poly-$C_1$–$C_8$-alkoxy-$C_1$–$C_8$-alkyl, each of which is optionally substituted by halogen; $C_3$–$C_8$-cycloalkyl in which one or more ring members that are not directly adjacent are optionally replaced by oxygen and/or sulphur and that is optionally substituted by halogen, $C_1$–$C_6$-alkyl, or $C_1$–$C_6$-alkoxy; phenyl that is optionally substituted by halogen, cyano, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio, or $C_1$–$C_6$-alkylsulphonyl; phenyl-$C_1$–$C_6$-alkyl that is optionally substituted by halogen, nitro, cyano, $C_1C_6$-alkyl, $C_1$–$C_6$-alkoxy, $C_1$–$C_6$-halogeno-alkyl, or $C_1$–$C_6$-halogenoalkoxy; 5- or 6-membered hetaryl that is optionally substituted by halogen, $C_1$–$C_6$-alkyl, or trifluoromethyl; phenoxy-$C_1$–$C_6$-alkyl that is optionally substituted by halogen or $C_1$–$C_6$-alkyl; or 5- or 6-membered hetaryloxy-$C_1$–$C_6$-alkyl that is optionally substituted by halogen, amino, or $C_1$–$C_6$-alkyl, and $R^2$ represents $C_1$–$C_{20}$-alkyl, $C_2$–$C_{20}$-alkenyl, $C_1$–$C_8$-alkoxy-$C_2$–$C_8$-alkyl, or poly-$C_1$–$C_8$-alkoxy-$C_2$–$C_8$-alkyl, each of which is optionally substituted by halogen; $C_3$–$C_8$-cycloalkyl that is optionally substituted by halogen, $C_1$–$C_6$-alkyl, or $C_1$–$C_6$-alkoxy; or phenyl or benzyl, each of which is optionally substituted by halogen, cyano, nitro, $C_1$–$C_6$-alkyl, $C_1$–$C_6$-alkoxy, $C_1$–$C_6$-halogenoalkyl, or $C_1$–$C_6$-halogenalkoxy.

3. A compound of formula (I) according to claim 1 in which

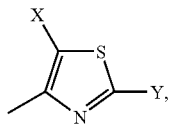

Het represents

W represents oxygen,

X represents hydrogen or $C_1$–$C_4$-alkyl;

Y represents chlorine, bromine, $C_1$–$C_4$-alkyl, $C_1$–$C_4$-halogenoalkyl, $C_1$–$C_4$-alkoxy, $C_1$–$C_4$-halogenoalkoxy, or a group

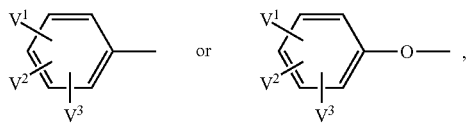

in which $V^1$ represents hydrogen, fluorine, chlorine, bromine, $C_1$–$C_6$-alkyl, $C_1$–$C_4$-alkoxy, $C_1$–$C_2$-halogenoalkyl, $C_1$–$C_2$-halogenalkoxy, nitro, or cyano; or phenyl, phenoxy, phenoxy-$_1$–$C_2$-alkyl, phenyl-$C_1$–$C_2$-alkoxy, phenyl-thio-$C_1$–$C_2$-alkyl, or phenyl-$C_1$–$C_2$-alkylthio, each of which is optionally monosubstituted or disubstituted by fluorine, chlorine, bromine, $C_1$–$C_4$-alkyl, $C_1$–$C_4$-alkoxy, $C_1$–$C_2$-halogenoalkyl, $C_1$–$C_2$-halogenalkoxy, nitro, or cyano, and $V^2$ represents hydrogen, fluorine, chlorine, bromine, $C_1$–$C_4$-alkyl, $C_1$–$C_4$-alkoxy, $C_1$–$C_2$-halogenoalkyl, or $C_1$–$C_2$-halogenalkoxy, or $V^1$ and $V^2$ together with the carbon atoms to which they are bonded represent a 5- or 6-membered cycle in which one or two carbon atoms is optionally replaced by oxygen and that is optionally substituted by fluorine or methyl, A represents hydrogen; $C_1$–$C_8$-alkyl or $C_1$–$C_4$-alkoxy-$_1$–$C_2$-alkyl, each of which is optionally substituted by fluorine; $C_5$–$C_6$-cycloalkyl or $C_3$–$C_6$-cycloalkyl-$C_1$–$C_2$-alkyl in which one ring member is optionally replaced by oxygen or sulphur and that is optionally substituted by fluorine, chlorine, methyl, ethyl, or methoxy; or phenyl or benzyl, each of which is optionally substituted by fluorine, chlorine, bromine, $C_1$–$C_4$-alkyl, $C_1$–$C_2$-halogenoalkyl, $C_1$–$C_4$-alkoxy, or $C_1$–$C_2$-halogenoalkoxy, B represents hydrogen or $C_1$–$C_4$-alkyl, or A, B, and the carbon atom to which they are bonded represent saturated $C_5$–$C_7$-cycloalkyl in which one ring member is optionally replaced by oxygen and that is optionally monosubstituted by $C_1$–$C_4$-alkyl, trifluoromethyl, or $C_1$–$C_4$-alkoxy, $Q^1$ represents hydrogen, $C_1$–$C_4$-alkyl, or $C_1$–$C_4$-alkoxy-$C_1$–$C_2$-alkyl; or $C_3$–$C_6$-cycloalkyl in which one methylene group is optionally replaced by oxygen and that is optionally substituted by methyl or methoxy, $Q^2$ represents hydrogen, methyl, or ethyl, or $Q^1$ and $Q^2$ together with the carbon atom to which they are bonded represent saturated $C_5$–$C_6$-cycloalkyl in which one ring member is optionally replaced by oxygen and that is optionally substituted by $C_1$–$C_4$-alkyl or $C_1$–$C_4$-alkoxy, and G represents hydrogen (a) or one of the groups (b)

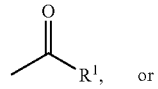

or (c)

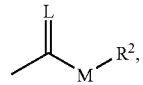

in which

L represents oxygen or sulphur,

M represents oxygen or sulphur, $R^1$ represents $C_1$–$C_{16}$-alkyl, $C_2$–$C_{16}$-alkenyl, $C_1$–$C_4$-alkoxy-$C_1$–$C_2$-alkyl, or $C_1$–$C_4$-alkylthio-$C_1$–$C_2$-alkyl, each of which is optionally substituted by fluorine or chlorine; $C_3$–$C_7$-cycloalkyl in which one or two ring members that are not directly adjacent are optionally replaced by oxygen and/or sulphur and that is optionally substituted by fluorine, chlorine, $C_1$–$C_5$-alkyl or $C_1$–$C_5$-alkoxy; phenyl that is optionally substituted by fluorine, chlorine, bromine, cyano, nitro, $C_1$–$C_4$-alkyl, $C_1$–$C_4$-alkoxy, trifluoromethyl, or trifluoromethoxy; or pyridyl or thienyl, each of which is optionally substituted by fluorine, chlorine, bromine, methyl, ethyl, or trifluoromethyl, and $R^2$ represents $C_1$–$C_{16}$-alkyl, $C_2$–$C_{16}$-alkenyl, or $C_1$–$C_4$-alkoxy-$C_2$–$C_4$-alkyl, each of which is optionally substituted by fluorine; $C_3$–$C_7$-cyclo-alkyl that is optionally substituted by methyl, ethyl or methoxy; or phenyl or benzyl, each of which is optionally substituted by fluorine, chlorine, bromine, cyano, nitro, $C_1$–$C_4$-alkyl, $C_1$–$C_3$-alkoxy, trifluoro-methyl, or trifluoromethoxy.

4. A compound of formula (I) according to claim 1 in which

Het represents

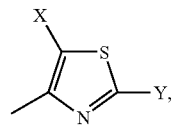

W represents oxygen,

X represents methyl, ethyl, n-propyl, isopropyl, n-butyl, or isobutyl,

Y represents methyl, ethyl, n-propyl, isopropyl, n-butyl, isobutyl, tert-butyl, or the group

in which

V¹ represents hydrogen, fluorine, chlorine, bromine, methyl, ethyl, n-propyl, isopropyl, n-butyl, isobutyl, tert-butyl, methoxy, ethoxy, n-propoxy, isopropoxy, trifluoromethyl, or trifluoromethoxy, and V² represents hydrogen, fluorine, chlorine, methyl, ethyl, n-propyl, isopropyl, methoxy, ethoxy, trifluoromethyl, or trifluoromethoxy, A represents hydrogen, methyl, ethyl, propyl, isopropyl, butyl, isobutyl, methoxymethyl, or ethoxymethyl, B represents hydrogen, methyl, or ethyl, or A, B, and the carbon atom to which they are bonded represent saturated $C_5$–$C_6$-cycloalkyl in which one ring member is optionally replaced by oxygen and that is optionally monosubstituted by methyl, ethyl, n-propyl, isopropyl, butyl, trifluoromethyl, methoxy, ethoxy, n-propoxy, or n-butoxy, Q¹ represents hydrogen, methyl, ethyl, propyl, isopropyl, cyclopropyl, cyclopentyl, or cyclohexyl, Q² represents hydrogen, methyl, or ethyl, or Q¹ and Q² jointly with the carbon to which they are bonded represent saturated $C_5$–$C_6$-cycloalkyl in which one ring member is optionally replaced by oxygen and that is optionally substituted by methyl, ethyl, propyl, isopropyl, methoxy, ethoxy, propoxy, or butoxy, G represents hydrogen (a) or one of the groups

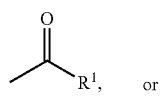
(b)

or

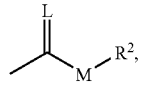
(c)

in which

L represents oxygen or sulphur,

M represents oxygen or sulphur,

R¹ represents $C_1$–$C_1$-alkyl, $C_2$–$C_{14}$-alkenyl, $C_1$–$C_4$-alkoxy-$C_1$–$C_2$-alkyl, or $C_1$–$C_4$-alkylthio-$C_1$–$C_2$-alkyl, each of which is optionally substituted by fluorine or chlorine; $C_3$–$C_6$-cycloalkyl in which one or two ring members that are not directly adjacent are optionally replaced by oxygen and/or sulphur and that is optionally substituted by fluorine, chlorine, methyl, ethyl, or methoxy; phenyl that is optionally substituted by fluorine, chlorine, bromine, cyano, nitro, methyl, ethyl, isopropyl, tert-butyl, methoxy, trifluoromethyl, or trifluoromethoxy; or thienyl or pyridyl, each of which is optionally substituted by fluorine, chlorine, bromine, or methyl, and R² represents $C_1$–$C_{14}$-alkyl, $C_2$–$C_{14}$-alkenyl, or $C_2$–$C_4$-alkoxy-$C_2$–$C_3$-alkyl, each of which is optionally substituted by fluorine; $C_3$–$C_6$-cycloalkyl that is optionally substituted by methyl, ethyl, or methoxy; or phenyl or benzyl, each of which is optionally substituted by fluorine, chlorine, cyano, nitro, methyl, ethyl, isopropyl, tert-butyl, methoxy, trifluoromethyl, or trifluoromethoxy.

5. A compound of formula (I) according to claim 1 in which

Het represents

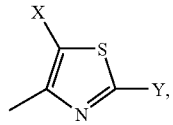

W represents oxygen,

X represents methyl, ethyl, n-propyl, or i-propyl,

Y represents

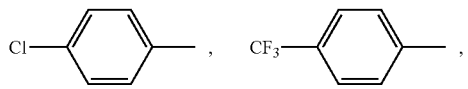

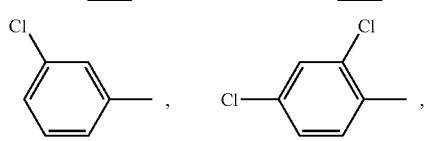

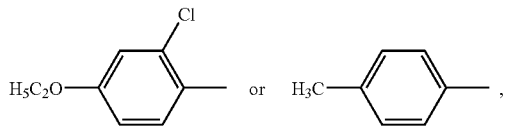

A represents hydrogen or methyl,

B represents hydrogen or methyl, or

A, B, and the carbon atom to which they are bonded represent saturated $C_6$-cycloalkyl in which one ring member is optionally replaced by oxygen, Q¹ represents hydrogen or methyl, Q² represents hydrogen or methyl, or Q¹ and Q² jointly with the carbon to which they are bonded represent saturated $C_6$-cycloalkyl in which one ring member is optionally replaced by oxygen, G represents hydrogen (a) or one of the groups

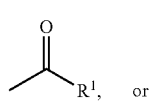
(b)

or

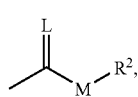
(c)

in which

M represents oxygen or sulphur,

R¹ represents $C_1$–$C_4$-alkyl, or $C_1$–$C_4$-alkoxy-$C_1$–$C_2$-alkyl; or phenyl or pyridyl, each of which is optionally substituted by chlorine, and R² represents $C_1$–$C_4$-alkyl, phenyl, or benzyl.

6. A process for the preparation of a compound of formula (I) according to claim 1 comprising (A) for substituted 5,6-dihydropyrones of formula (I-2-a)

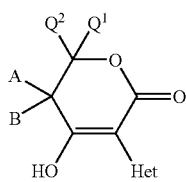
(I-2-a)

in which A, B, $Q^1$, $Q^2$, and Het have the meanings given for formula (I), subjecting to an intramolecular condensation reaction an O-acyl hydroxycarboxylic ester of formula (III)

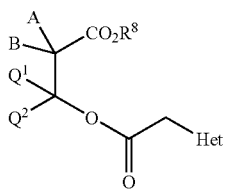
(III)

in which
A, B, $Q^1$, $Q^2$, and Het have the meanings given for formula (I), and
$R^8$ represents alkyl,
in the presence of a diluent and in the presence of a base, (B) for compounds of formula (I-2-b)

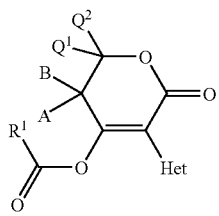
(I-2-b)

in which A, B, $Q^1$, $Q^2$, $R^1$, and Het have the meanings given for formula (I), reacting a compound of the formulas (I-2-a) with
(α) an acid halide of formula (IV)

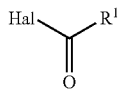
(IV)

in which
$R^1$ has the meanings given for formula (I), and
Hal represents halogen, or
(β) a carboxylic anhydride of the formula (V)

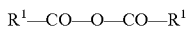
$R^1$—CO—O—CO—$R^1$ (V)

in which $R^1$ has the meanings given for formula (I), optionally in the presence of a diluent and optionally in the presence of an acid binder;

(C) for-compounds of formula (I-2-c)

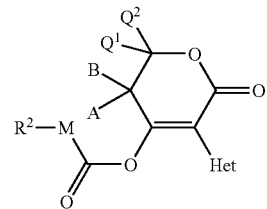
(I-2-c)

in which
A, B, $Q^1$, $Q^2$, $R^2$, M, and Het have the meanings given for formula (I), and
L represents oxygen, reacting a compound of the formulas (I-2-a) with a chloroformic ester or a chloroformic thioester of formula (VI)

$R^2$-M-CO—Cl (VI)

in which $R^2$ and M have the meanings given for formula (I), optionally in the presence of a diluent and optionally in the presence of an acid binder; or (D) for compounds of formulas (I-2-c)

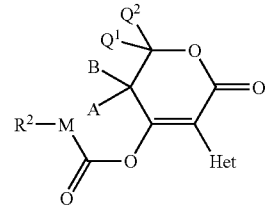
(I-2-c)

in which
A, B, $Q^1$, $Q^2$, $R^2$, M, and Het have the meanings given for formula (I), and
L represents sulphur, reacting a compound of the formulas (I-2-a) with a chloromonothioformic ester or a chlorodithioformic ester of formula (VII)

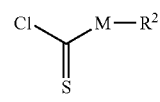
(VII)

in which $R^2$ and M have the meanings given for formula (I), optionally in the presence of a diluent and optionally in the presence of an acid binder.

7. A pesticide, microbicide, or herbicide comprising an effective amount of a compound of formula (I) according to claim 1 and one or more extenders and/or surfactants.

8. A method of controlling animal pests comprising allowing an effective amount of a compound of formula (I) according to claim 1 to act on the pests and/or their environment.

9. A method of controlling undesired vegetation comprising allowing an effective amount of a compound of formula (I) according to claim 1 to act on the undesired vegetation and/or its environment.

10. A method of controlling fungi comprising allowing an effective amount of a compound of formula (I) according to claim 1 to act on the fungi and/or their environment.

11. A process for the preparation of a pesticide, microbicide, or herbicide comprising mixing a compound of formula (I) according to claim 1 with one or more extenders and/or surfactants.

* * * * *